US006641798B2

(12) United States Patent
Achilefu et al.

(10) Patent No.: US 6,641,798 B2
(45) Date of Patent: *Nov. 4, 2003

(54) TUMOR-TARGETED OPTICAL CONTRAST AGENTS

(75) Inventors: Samuel I. Achilefu, St. Louis, MO (US); Raghavan Rajagopalan, Maryland Heights, MO (US); Richard B. Dorshow, St. Louis, MO (US); Joseph E. Bugaj, St. Charles, MO (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/863,971

(22) Filed: May 23, 2001

(65) Prior Publication Data

US 2002/0044909 A1 Apr. 18, 2002

Related U.S. Application Data

(63) Continuation-in-part of application No. 09/484,320, filed on Jan. 18, 2000, now Pat. No. 6,180,087.

(51) Int. Cl.[7] .......................... A61B 10/00; A61B 5/00; A61B 8/00
(52) U.S. Cl. ....................... 424/9.6; 548/400; 548/416; 548/427
(58) Field of Search .............................. 424/1.11, 1.65, 424/9.1, 9.6, 9.3, 9.4, 9.5; 548/400, 427, 416

(56) References Cited

U.S. PATENT DOCUMENTS

| | | | | |
|---|---|---|---|---|
| 5,453,505 | A | 9/1995 | Lee et al. | 544/124 |
| 5,672,333 | A | 9/1997 | Rajagopalan et al. | 424/9.6 |
| 5,709,845 | A | 1/1998 | Rajagopalan et al. | 424/9.6 |
| 5,732,104 | A | 3/1998 | Brown et al. | 375/222 |
| 6,180,087 | B1 * | 1/2001 | Achilefu et al. | 424/9.6 |
| 6,264,920 | B1 * | 7/2001 | Achilefu et al. | 424/9.6 |

FOREIGN PATENT DOCUMENTS

| | | | | |
|---|---|---|---|---|
| WO | WO9617628 | 6/1996 | .......... | A61K/49/00 |
| WO | WO9822146 | 5/1998 | .......... | A61K/49/00 |
| WO | WO9844838 | 10/1998 | .......... | A47L/13/258 |
| WO | WO9844846 | 10/1998 | .......... | A61B/5/117 |

OTHER PUBLICATIONS

M. Brinkley, *A Brief Survey of Methods for Preparing Protein Conjugates with Dyes, Haptens, and Cross–Linking Reagents*, American Chemical Society, Reprinted from Bioconjugate Chemistry, vol. 3, No. 1, Jan./Feb. 1992, 59–70.
J. Caesar et al., *The Use of Indocyanine Green in the Measurement of Hepatic Blood Flow and As a Test of Hepatic Function*, Clin. Sci., 21, 1961, 43–57.
G.R. Cherrick et al., *Indocyanine Green: Observations on Its Physical Properties, Plasma Decay, and Hepatic Extraction*, J. Clinical Investigation, 39, 1960, 592–600.
M. de Jong et al., *Comparison of 111In–labeled Somatostatin Analogues for Tumor Scintigraphy and Radionuclide Therapy*, Cancer Research., 58, Feb. 1, 1988, 437–441.
J.H. Flanagan, Jr. et al., *Near–Infrared Heavy–Atom–Modified Fluorescent Dyes for Base–Calling in DNA–Sequencing Applications Using Temporal Discrimination*, Anal. Chem., 70:13, Jul. 1, 1998, 2676–2684.
Y–L He et al., *Measurement of Blood Volume Using Indocyanine Green Measured with Pulse–Spectrophotometry: Its Reproducibility and Reliability*, Critical Care Medicine, 26:8, 1998, 1446–1451.
R.K. Jain, *Barriers to Drug Delivery in Solid Tumors*, Scientific American, Jul., 1994, 58–65.
R.B. Mujumdar et al., *Cyanine Dye Labeling Reagents: Sulfoindocyanine Succinimidyl Esters*, Bioconjugate Chemistry, 4:2, Mar./Apr. 1993, 105–111.
N. Narayanan et al., *A New Method for the Synthesis of Heptamethine Cyanine Dyes: Synthesis of New Near–Infrared Fluorescent Labels*. J. Org. Chem. 60, 1995, 2391–2395.
G. Patonay et al., *Near–Infrared Fluorogenic Labels: New Approach to an Old Problem*, Analytical Chemistry, 63, 1991, 321A–322A.
G.A. Reynolds et al., *Stable Heptamethine Pyrylium Dyes That Absorb in the Infrared*, J. Org. Chem., 42:5, 885–888.
J. Slavik, *Fluorescent Probes in Cellular and Molecular Biology*, CRC Press, Inc., Boca Raton, Florida, 1994.
P.L. Southwick et al., *"One Pot" Fischer Synthesis of (2,3,3–trimethyl–3–H–indol–5–yl)–Acetic Acid, Derivatives as Intermediates for Fluorescent Biolabels*, Org. Prep. Proced. Int. Briefs, 20:3, 1988, 279–284.
L. Strekowski et al., *Substitution Reactions of a Nucleofugal Group in Heptamethine Cyanine Dyes. Synthesis of an Isothiocyanato Derivative for Labeling of Proteins with a Near–Infrared Chromophore*, J. Org. Chem., 57, 1992, 4578–4580.
B.C. Wilson, *Optical Properties of Tissue*, Encyclopedia of Human Biology, Sec. Ed., vol. 6, Academic Press, 1991, 451–461..

* cited by examiner

Primary Examiner—Dameron L. Jones
(74) Attorney, Agent, or Firm—Wood, Herron & Evans, L.L.P.

(57) ABSTRACT

Cyanine dye bioconjugates useful for diagnostic imaging and therapy are disclosed. The conjugates include several cyanine dyes with a variety of bis- and tetrakis (carboxylic acid) homologes. The compounds may be conjugated to bioactive peptides, carbohydrates, hormones, drugs, or other bioactive agents. The small size of the compounds allows more favorable delivery to tumor cells as compared to larger molecular weight imaging agents. The various dyes are useful over the range of 350 to 1,300 nm, the exact range being dependent upon the particular dye. The use of dimethylsulfoxide helps to maintain the fluorescence of the compounds. The inventive compounds are useful for diagnostic imaging and therapy, in endoscopic applications for the detection of tumors and other abnormalities, for localized therapy, for photoacoustic tumor imaging, detection and therapy, and for sonofluorescence tumor imaging, detection and therapy.

20 Claims, 14 Drawing Sheets

(4 of 14 Drawing Sheet(s) Filed in Color)

TUMOR-TARGETED OPTICAL CONTRAST AGENTS

This application is a continuation-in-part of application Ser. No. 09/484,320 filed Jan. 18, 2000 now U.S. Pat. No. 6,180,087.

FIELD OF INVENTION

This invention relates generally to compositions of cyanine dye bioconjugates with bioactive molecules for diagnosis and therapy, and particularly for visualization and detection of tumors.

BACKGROUND OF THE INVENTION

Several dyes that absorb and emit light in the visible and near-infrared region of electromagnetic spectrum are currently being used for various biomedical applications due to their biocompatibility, high molar absorptivity, and/or high fluorescence quantum yields. The high sensitivity of the optical modality in conjunction with dyes as contrast agents parallels that of nuclear medicine, and permits visualization of organs and tissues without the undesirable effect of ionizing radiation.

Cyanine dyes with intense absorption and emission in the near-infrared (NIR) region are particularly useful because biological tissues are optically transparent in this region (B. C. Wilson, Optical properties of tissues. *Encyclopedia of Human Biology*, 1991, 5, 587–597). For example, indocyanine green, which absorbs and emits in the NIR region, has been used for monitoring cardiac output, hepatic functions, and liver blood flow (Y-L. He, et al., Measurement of blood volume using indocyanine green measured with pulse-spectrometry: Its reproducibility and reliability. *Critical Care Medicine*, 1998, 26(8), 1446–1451; J. Caesar, et al., The use of Indocyanine green in the measurement of hepatic blood flow and as a test of hepatic function. *Clin. Sci.* 1961, 21, 43–57), and its functionalized derivatives have been used to conjugate biomolecules for diagnostic purposes (R. B. Mujumdar, et al., Cyanine dye labeling reagents: Sulformdocyanine succinimidyl esters. *Bioconjugate Chemistry*, 1993, 4(2), 105–111; U.S. Pat. No. 5,453,505; WO 98/48846; WO 98/22146; WO 96/17628; WO 98/48838).

A major drawback in the use of cyanine dye derivatives is the potential for hepatobiliary toxicity resulting from the rapid clearance of these dyes by the liver (G. R. Cherrick, et al., Indocyanine green: Observations on its physical properties, plasma decay, and hepatic extraction. *J. Clinical Investigation*, 1960, 39, 592–600). This is associated with the tendency of cyanine dyes in solution to form aggregates, which could be taken up by Kupffer cells in the liver.

Various attempts to obviate this problem have not been very successful. Typically, hydrophilic peptides, polyethyleneglycol or oligosaccharide conjugates have been used, but these resulted in long-circulating products, which are eventually still cleared by the liver. Another major difficulty with current cyanine and indocyanine dye systems is that they offer a limited scope in the ability to induce large changes in the absorption and emission properties of these dyes. Attempts have been made to incorporate various heteroatoms and cyclic moieties into the polyene chain of these dyes (L. Strekowski, et al., Substitution reactions of a nucleofugal group in hetamethine cyanine dyes. *J. Org. Chem.*, 1992, 57, 4578–4580; N. Narayanan, and G. Patonay, A new method for the synthesis of heptamethine cyanine dyes: Synthesis of new near infrared fluorescent labels. *J. Org. Chem.*, 1995, 60, 2391–2395; U.S. Pat. Nos. 5,732,104; 5,672,333; and 5,709,845), but the resulting dye systems do not show large differences in absorption and emission maxima, especially beyond 830 nm where photoacoustic diagnostic applications are very sensitive. They also possess a prominent hydrophobic core, which enhances liver uptake. Further, most cyanine dyes do not have the capacity to form starburst dendrimers, which are useful in biomedical applications.

For the purpose of tumor detection, many conventional dyes are useful for in vitro applications because of their highly toxic effect on both normal and abnormal tissues. Other dyes lack specificity for particular organs or tissues and, hence, these dyes must be attached to bioactive carriers such as proteins, peptides, carbohydrates, and the like to deliver the dyes to specific regions in the body. Several studies on the use of near infrared dyes and dye-biomolecule conjugates have been published (G. Patonay and M. D. Antoine, Near-infrared Fluorogenic Labels: New Approach to an Old Problem, *Analytical Chemistry*, 1991, 63:321A-327A and references therein; M. Brinkley, A Brief Survey of Methods for Preparing Protein Conjugates with Dyes, Haptens, and Cross-Linking Reagents, *Perspectives in Bioconjugate Chemistry* 1993, pp. 59–70, C. Meares (Ed), ACS Publication, Washington, D.C.; J. Slavik, *Fluorescent Probes in Cellular and Molecular Biology*, 1994, CRC Press, Inc.; U.S. Pat. No. 5,453,505; WO 98/48846; WO 98/22146; WO 96/17628; WO 98/48838). Of particular interest is the targeting of tumor cells with antibodies or other large protein carriers such as transferrin as delivery vehicles (A. Becker, et al., "Transferrin Mediated Tumor Delivery of Contrast Media for Optical Imaging and Magnetic Resonance Imaging", Biomedical Optics meeting, Jan. 23–29, 1999, San Jose, Calif.). Such an approach has been widely used in nuclear medicine applications. Its major advantage is the retention of a carrier's tissue specificity, since the molecular volume of the dye is substantially smaller than the carrier. However, this approach does have some serious limitations in that the diffusion of high molecular weight bioconjugates to tumor cells is highly unfavorable, and is further complicated by the net positive pressure in solid tumors (R. K. Jain, Barriers to Drug Delivery in Solid Tumors, *Scientific American* 1994, 271:58–65. Furthermore, many dyes in general, and cyanine dyes, in particular, tend to form aggregates in aqueous media that lead to fluorescence quenching.

Therefore, there is a need for dyes that could prevent dye aggregation in solution, that are predisposed to form dendrimers, that are capable of absorbing or emitting beyond 800 nm, that possess desirable photophysical properties, and that are endowed with tissue-specific targeting capability.

SUMMARY OF THE INVENTION

The invention is directed to compositions, and methods of preparing the compositions, of low molecular weight biomolecule-dye conjugates to enhance tumor detection. The inventive compositions preserve the fluorescence efficiency of the dye molecules, do not aggregate in solution, form starburst dendrimers, are capable of absorbing or omitting light in the near infrared region (beyond 800 mm), and can be rendered tissue-specific.

In one embodiment, the inventive composition comprises cyanine dyes of general formula 1.

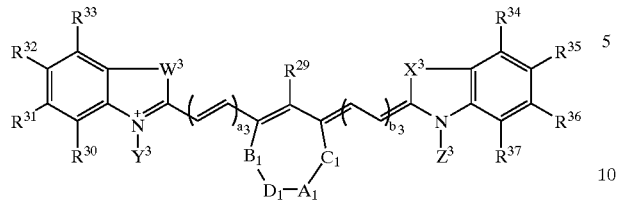

wherein $W^3$ and $X^3$ may be the same or different and are selected from the group consisting of —$CR^1R^2$, —O—, —$NR^3$, —S—, and —Se; $Y^3$ is selected from the group consisting of —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—$N(R^3)$—$(CH_2)_b$—CONH—Bm, $(CH_2)_a$—N$(R^3)$—$(CH_2)_c$—NHCO—Bm, —$(CH_2)_a$—$N(R^3)$—$CH_2$—$(CH_2OCH_2)_b$—$CH_2$—CONH—Bm, —$(CH_2)_a$—$N(R^3)$—$CH_2$—$(CH_2OCH_2)_b$—$CH_2$—NHCO—Bm, —$CH_2$—$(CH_2OCH_2)_b$—$CH_2$—$N(R^3)$—$(CH_2)_a$—CONH—Bm, —$CH_2$—$(CH_2OCH_2)_b$—$CH_2$—$N(R^3)$—$(CH_2)_a$—NHCO—Bm, —$CH_2$—$(CH_2OCH_2)_b$—$CH_2$—$N(R^3)$—$CH_2$—$(CH_2OCH_2)_d$—CONH—Bm, —$CH_2$—$(CH_2OCH_2)_b$—$CH_2$—$N(R^3)$—$CH_2$—$(CH_2OCH_2)_d$—NHCO—Bm, —$(CH_2)_a$—$NR^3R^4$, and —$CH_2(CH_2OCH_2)_b$—$CH_2NR^3R^4$; $Z^3$ is selected from the group consisting of —$(CH_2)_a$—CONH—Dm, —$CH_2$—$(CH_2OCH_2)_b$—$CH_2$—CONH—Dm, —$(CH_2)_a$—NHCO—Dm, —$CH_2$—$(CH_2OCH_2)_b$—$CH_2$—NHCO—Dm, —$(CH_2)_a$—$N(R^3)$—$(CH_2)_b$—CONH—Dm, $(CH_2)_a$—N$(R^3)$—$(CH_2)_c$—NHCO—Dm, —$(CH_2)_a$—$N(R^3)$—$CH_2$—$(CH_2OCH_2)_b$—$CH_2$—CONH—Dm, —$(CH_2)_a$—$N(R^3)$—$CH_2$—$(CH_2OCH_2)_b$—$CH_2$—NHCO—Dm, —$CH_2$—$(CH_2OCH_2)_b$—$CH_2$—$N(R^3)$—$(CH_2)_a$—CONH—Dm, —$CH_2$—$(CH_2OCH_2)_b$—$CH_2$—$N(R^3)$—$(CH_2)_a$—NHCO—Dm, —$CH_2$—$(CH_2OCH_2)_b$—$CH_2$—$N(R^3)$—$CH_2$—$(CH_2OCH_2)_d$—CONH—Dm, —$CH_2$—$(CH_2OCH_2)_b$—$CH_2$—$N(R^3)$—$CH_2$—$(CH_2OCH_2)_d$—NHCO—Dm, —$(CH_2)_a$—$NR^3R^4$, and —$CH_2(CH_2OCH_2)_b$—$CH_2NR^3R$ different and are selected from the group consisting of —O—, —S—, —Se—, —P—, —$CR^1R^2$, —$CR^1$, alkyl, $NR^3$, and —C=O; $A_1$, $B_1$, $C_1$, and $D_1$ may together form a 6- to 12-membered carbocyclic ring or a 6- to 12-membered heterocyclic ring optionally containing one or more oxygen, nitrogen, or sulfur atom; $a_3$ and $b_3$ independently vary from 0 to 5; $R^1$ to $R^4$, and $R^{29}$ to $R^{37}$ are independently selected from the group consisting of hydrogen, $C_1$–$C_{10}$ alkyl, $C_5$–$C_{20}$ aryl, $C_1$–$C_{10}$ alkoxyl, $C_1$–$C_{10}$ polyalkoxyalkyl, $C_1$–$C_{20}$ polyhydroxyalkyl, $C_5$–$C_{20}$ polyhydroxyaryl, $C_1$–$C_{10}$ aminoalkyl, cyano, nitro, halogen, saccharide, peptide, —$CH_2(CH_2OCH_2)_b$—$CH_2$—OH, —$(CH_2)_a$—$CO_2H$, —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—OH and —$CH_2$—$(CH_2OCH_2)_b$—$CO_2H$; Bm and Dm are independently selected from the group consisting of a bioactive peptide, a protein, a cell, an antibody, an antibody fragment, a saccharide, a glycopeptide, a peptidomimetic, a drug, a drug mimic, a hormone, a metal chelating agent, a radioactive or nonradioactive metal complex, and an echogenic agent; a and c are independently from 1 to 20; and b and d are independently from 1 to 100.

In a second embodiment, the inventive composition comprises cyanine dyes of general formula 2.

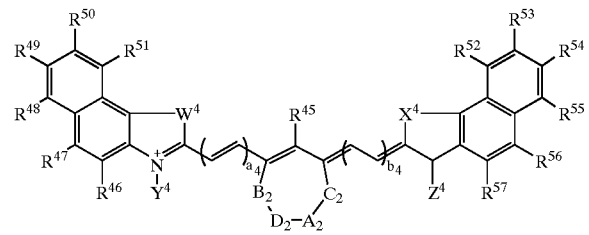

wherein $W^4$ and $X^4$ may be the same or different and are selected from the group consisting of —$CR^1R^2$, —O—, —$NR^3$, —S—, and —Se; $Y^4$ is selected from the group consisting of —$(CH_2)_a$—CONH—Bm, —$CH_2$—$(CH_2OCH_2)_b$—$CH_2$—CONH—Bm, —$(CH_2)$—NHCO—Bm, —$CH_2$—$(CH_2OCH_2)_b$—$CH_2$—NHCO—Bm, —$(CH_2)_a$—$N(R^3)$—$(CH_2)_b$—CONH—Bm, $(CH_2)_a$—N$(R^3)$—$(CH_2)_c$—NHCO—Bm, —$(CH_2)_a$—$N(R^3)$—$CH_2$—$(CH_2OCH_2)_b$—$CH_2$—CONH—Bm, —$(CH_2)_a$—$N(R^3)$—$CH_2$—$(CH_2OCH_2)_b$—$CH_2$—NHCO—Bm, —$CH_2$—$(CH_2OCH_2)_b$—$CH_2$—$N(R^3)$—$(CH_2)_a$—CONH—Bm, —$CH_2$—$(CH_2OCH_2)_b$—$CH_2$—$N(R^3)$—$(CH_2)_a$—NHCO—Bm, —$CH_2$—$(CH_2OCH_2)_b$—$CH_2$—$N(R^3)$—$CH_2$—$(CH_2OCH_2)_d$—CONH—Bm, —$CH_2$—$(CH_2OCH_2)_b$—$CH_2$—$N(R^3)$—$CH_2$—$(CH_2OCH_2)_d$—NHCO—Bm, —$(CH_2)_a$—$NR^3R^4$, and —$CH_2(CH_2OCH_2)_b$—$CH_2NR^3R^4$; $Z^4$ is selected from the group consisting of —$(CH_2)$—CONH—Dm, —$CH_2$—$(CH_2OCH_2)_b$—$CH_2$—CONH—Dm, —$(CH_2)_a$—NHCO—Dm, —$CH_2$—$(CH_2OCH_2)_b$—$CH_2$—NHCO—Dm, —$(CH_2)_a$—$N(R^3)$—$(CH_2)_b$—CONH—Dm, $(CH_2)_a$—N$(R^3)$—$(CH_2)_c$—NHCO—Dm, —$(CH_2)_a$—$N(R^3)$—$CH_2$—$(CH_2OCH_2)_b$—$CH_2$—CONH—Dm, —$(CH_2)_a$—$N(R^3)$—$CH_2$—$(CH_2OCH_2)_b$—$CH_2$—NHCO—Dm, —$CH_2$—$(CH_2OCH_2)_b$—$CH_2$—$N(R^3)$—$(CH_2)_a$—CONH—Dm, —$CH_2$—$(CH_2OCH_2)_b$—$CH_2$—N$(R^3)$—$(CH_2)_a$—NHCO—Dm, —$CH_2$—$(CH_2OCH_2)_b$—$CH_2$—$N(R^3)$—$CH_2$—$(CH_2OCH_2)_d$—CONH—Dm, —$CH_2$—$(CH_2OCH_2)_b$—$CH_2$—$N(R^3)$—$CH_2$—$(CH_2OCH_2)_d$—NHCO—Dm, —$(CH_2)_a$—$NR^3R^4$, and —$CH_2(CH_2OCH_2)_b$—$CH_2NR^3R^4$; $A_2$ is a single or a double b or different and are selected from the group consisting of —O—, —S—, —Se—, —P—, —$CR^1R^2$, —$CR^1$, alkyl, $NR^3$, and —C=O; $A_2$, $B_2$, $C_2$, and $D_2$ may together form a 6- to 12-membered carbocyclic ring or a 6- to 12-membered heterocyclic ring optionally containing one or more oxygen, nitrogen, or sulfur atom; $a_4$ and $b_4$ independently vary from 0 to 5; $R^1$ to $R^4$, and $R^{45}$ to $R^{57}$ are independently selected from the group consisting of hydrogen, $C_1$–$C_{10}$ alkyl, $C_5$–$C_{20}$ aryl, $C_1$–$C_{10}$ alkoxyl, $C_1$–$C_{10}$ polyalkoxyalkyl, $C_1$–$C_{20}$ polyhydroxyalkyl, $C_5$–$C_{20}$ polyhydroxyaryl, $C_1$–$C_{10}$ aminoalkyl, cyano, nitro, halogen, saccharide, peptide, —$CH_2(CH_2OCH_2)_b$—$CH_2$—OH, —$(CH_2)_a$—$CO_2H$, —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—OH and —$CH_2$—$(CH_2OCH_2)_b$—$CO_2H$; Bm and Dm are independently selected from the group consisting of a bioactive peptide, a protein, a cell, an antibody, an antibody fragment, a saccharide, a glycopeptide, a peptidomimetic, a drug, a drug mimic, a hormone, a metal chelating agent, a radioactive or nonradioactive metal complex, and an echogenic agent; a and c are independently from 1 to 20; and b and d are independently from 1 to 100.-

In a third embodiment, the inventive composition comprises cyanine dyes of general formula 3

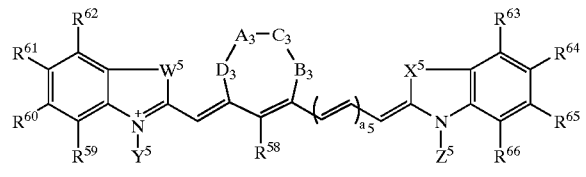

wherein $W^5$ and $X^5$ may be the same or different and are selected from the group consisting of —$CR^1R^2$, —O—, —$NR^3$, —S—, and —Se; $Y^5$ is selected from the group consisting of —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—N($R^3$)—$(CH_2)_b$—CONH—Bm, $(CH_2)_a$—N($R^3$)—$(CH_2)_c$—NHCO—Bm, —$(CH_2)_a$—N($R^3$)—$(CH_2)_b$—$CH_2$—CONH—Bm, —$(CH_2)$, —N($R^3$)—$CH_2$—$(CH_2OCH_2)_b$—$CH_2$—NHCO—Bm, —$CH_2$—$(CH_2OCH_2)_b$—$CH_2$—N($R^3$)—$(CH_2)_a$—CONH—Bm, —$CH_2$—$(CH_2OCH_2)_b$—$CH_2$—N($R^3$)—$(CH_2)_a$—NHCO—Bm, —$CH_2$—$(CH_2OCH_2)_b$—$CH_2$—N($R^3$)—$CH_2$—$(CH_2OCH_2)_d$—CONH—Bm, —$CH_2$—$(CH_2OCH_2)_b$—$CH_2$—N($R^3$)—$CH_2$—$(CH_2OCH_2)_d$—NHCO—Bm, —$(CH_2)_a$—$NR^3R^4$, and —$CH_2(CH_2OCH_2)_b$—$CH_2NR^3R^4$; $Z^5$ is selected from the group consisting of —$(CH_2)_a$—CONH—Dm, —$CH_2$—$(CH_2OCH_2)_b$—$CH_2$—CONH—Dm, —$(CH_2)_a$—NHCO—Dm, —$CH_2$—$(CH_2OCH_2)_b$—$CH_2$—NHCO—Dm, —$(CH_2)_a$—N($R^3$)—$(CH_2)_b$—CONH—Dm, $(CH_2)_a$—N($R^3$)—$(CH_2)_c$—NHCO—Dm, —$(CH_2)$—N($R^3$)—$CH_2$—$(CH_2OCH_2)_b$—$CH_2$—CONH—Dm, —$(CH_2)_a$—N($R^3$)—$CH_2$—$(CH_2OCH_2)_b$—$CH_2$—NHCO—Dm, —$CH_2$—$(CH_2OCH_2)_b$—$CH_2$—N($R^3$)—$(CH_2)_a$—CONH—Dm, —$CH_2$—$(CH_2OCH_2)_b$—$CH_2$—N($R^3$)—$(CH_2)_a$—NHCO—Dm, —$CH_2$—$(CH_2OCH_2)_b$—$CH_2$—N($R^3$)—$CH_2$—$(CH_2OCH_2)_d$—CONH—Dm, —$CH_2$—$(CH_2OCH_2)_b$—$CH_2$—N($R^3$)—$CH_2$—$(CH_2OCH_2)_d$—NHCO—Dm, —$(CH_2)_a$—$NR^3R^4$, and —$CH_2(CH_2OCH_2)_b$—$CH_2NR^3R^4$; $A_3$ is a single or a double bond; $B_3$, $C_3$ or different and are selected from the group consisting of —O—, —S—, —Se—, —P—, —$CR^1R^2$, —$CR^1$, alkyl, $NR^3$, and —C=O; $A_3$, $B_3$, $C_3$, and $D_3$ may together form a 6- to 12-membered carbocyclic ring or a 6- to 12-membered heterocyclic ring optionally containing one or more oxygen, nitrogen, or sulfur atom; $a_5$ is independently from 0 to 5; $R^1$ to $R^4$, and $R^{58}$ to $R^{66}$ are independently selected from the group consisting of hydrogen, $C_1$-$C_{10}$ alkyl, $C_5$-$C_{20}$ aryl, $C_1$-$C_{10}$ alkoxyl, $C_1$-$C_{10}$ polyalkoxyalkyl, $C_1$-$C_{20}$ polyhydroxyalkyl, $C_5$-$C_{20}$ polyhydroxyaryl, $C_1$-$C_{10}$ aminoalkyl, cyano, nitro, halogen, saccharide, peptide, —$CH_2(CH_2OCH_2)_b$—$CH_2$—OH, —$(CH_2)_a$—$CO_2H$, —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—OH and —$CH_2$—$(CH_2OCH_2)_b$—$CO_2H$; Bm and Dm are independently selected from the group consisting of a bioactive peptide, a protein, a cell, an antibody, an antibody fragment, a saccharide, a glycopeptide, a peptidomimetic, a drug, a drug mimic, a hormone, a metal chelating agent, a radioactive or nonradioactive metal complex, and an echogenic agent; a and c are independently from 1 to 20; and b and d are independently from 1 to 100.

In a fourth embodiment, the inventive composition comprises cyanine dyes of general formula 4

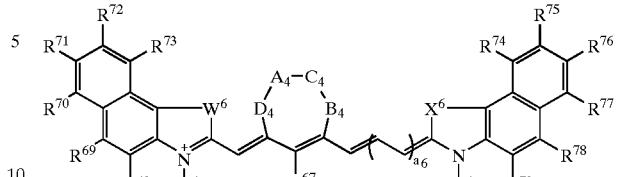

wherein $W^6$ and $X^6$ may be the same or different and are selected from the group consisting of —$CR^1R^2$, —O—, —$NR^3$, —S—, and —Se; $Y^6$ is selected from the group consisting of —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—N($R^3$)—$(CH_2)_b$—CONH—Bm, $(CH_2)_a$—N($R^3$)—$(CH_2)_c$—NHCO—Bm, —$(CH_2)_a$—N($R^3$)—$CH_2$—$(CH_2OCH_2)_b$—$CH_2$—CONH—Bm, —$(CH_2)_a$—N($R^3$)—$CH_2$—$(CH_2OCH_2)_b$—$CH_2$—NHCO—Bm, —$CH_2$—$(CH_2OCH_2)_b$—$CH_2$—N($R^3$)—$(CH_2)_a$-CONH—Bm, —$CH_2$—$(CH_2OCH_2)_b$—$CH_2$—N($R^3$)—$(CH_2)_a$—NHCO—Bm, —$CH_2$—$(CH_2CH_2)_b$—$CH_2$—N($R^3$)—$CH_2$—$(CH_2OCH_2)_d$—CONH—Bm, $CH_2$—$(CH_2OCH_2)_b$—$CH_2$—N($R^3$)—$CH_2$—$(CH_2OCH_2)_d$—NHCO—Bm, —$(CH_2)_a$—$NR^3R^4$, and —$CH_2(CH_2CH_2)_b$—$CH_2NR^3R^4$; $Z^6$ is selected from the group consisting of —$(CH_2)_a$—CONH—Dm, —$CH_2$—$(CH_2OCH_2)_b$—$CH_2$—CONH—Dm, —$(CH_2)_a$—NHCO—Dm, —$CH_2$—$(CH_2OCH_2)_b$—$CH_2$—NHCO—Dm, —$(CH_2)_a$—N($R^3$)—$(CH_2)_b$—CONH—Dm, $(CH_2)_a$—N($R^3$)—$(CH_2)_c$—NHCO—Dm, —$(CH_2)$—N($R^3$)—$CH_2$—$(CH_2OCH_2)_b$—$CH_2$—CONH—Dm, —$(CH_2)_a$—N($R^3$)—$CH_2$—$(CH_2OCH_2)_b$—$CH_2$—NHCO—Dm, —$CH_2$—$(CH_2OCH_2)_b$—$CH_2$—N($R^3$)—$(CH_2)_a$—CONH—Dm, —$CH_2$—$(CH_2OCH_2)_b$—$CH_2$—N($R^3$)—$(CH_2)_a$—NHCO—Dm, —$CH_2$—$(CH_2OCH_2)_b$—$CH_2$—N($R^3$)—$CH_2$—$(CH_2OCH_2)_d$—CONH—Dm, —$CH_2$—$(CH_2OCH_2)_b$—$CH_2$—N($R^3$)—$CH_2$—$(CH_2OCH_2)_d$—NHCO—Dm, —$(CH_2)_a$—$NR^3R^4$, and —$CH_2(CH_2OCH_2)_b$—$CH_2NR^3R^4$; $A_4$ is a single or a double bond; $B_4$, $C_4$, and $D_4$ may be the same or different and are selected from the group consisting of —O—, —S—, —Se—, —P—, —$CR^1R^2$, —$CR^1$, alkyl, $NR^3$, and —C=O; $A_4$, $B_4$, $C_4$, and $D_4$ may together form a 6- to 12-membered carbocyclic ring or a 6- to 12-membered heterocyclic ring optionally containing one or more oxygen, nitrogen, or sulfur atom; $a_6$ is independently from 0 to 5; $R^1$ to $R^4$, and $R^{67}$ to $R^{79}$ are independently selected from the group consisting of hydrogen, $C_1$-$C_{10}$ alkyl, $C_5$-$C_{20}$ aryl, $C_1$-$C_{10}$ alkoxyl, $C_1$-$C_{10}$ polyalkoxyalkyl, $C_1$-$C_{20}$ polyhydroxyalkyl, $C_5$-$C_{20}$ polyhydroxyaryl, $C_1$-$C_{10}$ aminoalkyl, cyano, nitro, halogen, saccharide, peptide, —$CH_2(CH_2OCH_2)_b$—$CH_2$—OH, —$(CH_2)_a$—$CO_2H$, —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—OH or —$CH_2$—$(CH_2OCH_2)_b$—$CO_2H$; Bm and Dm are independently selected from the group consisting of a bioactive peptide, a protein, a cell, an antibody, an antibody fragment, a saccharide, a glycopeptide, a peptidomimetic, a drug, a drug mimic, a hormone, a metal chelating agent, a radioactive or nonradioactive metal complex, and an echogenic agent; a and c are independently from 1 to 20; and b and d are independently from 1 to 100.

The invention will be further appreciated in light of the following figures, detailed description, and examples.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

DETAILED DESCRIPTION OF THE INVENTION

The novel compositions of the present invention comprising dyes of formulas 1 to 4 offer significant advantages over those currently described in the art. These inventive dyes form starburst dendrimers which prevent aggregation in solution by preventing intramolecular and intermolecular ordered hydrophobic interactions, and have multiple attachment sites proximal to the dye chromophore for ease of forming bioactive molecules. The presence of rigid and extended chromophore backbone enhances their fluorescence quantum yield and extends their maximum absorption beyond 800 nm. Conjugation of biomolecules to these dyes is readily achievable.

The inventive bioconjugates of the present invention also exploit the symmetric nature of the cyanine and indocyanine dye structures by incorporating one to ten receptor targeting groups in close proximity to each other, such that the receptor binding can be greatly enhanced due to a cooperative effect. Accordingly, several cyanine dyes containing one or more targeting domains have been prepared and tested in vivo for biological activity.

The inventive dye-bioconjugates of formulas 1 to 4 are useful for various biomedical applications. These include, but are not limited to, tomographic imaging of organs, monitoring of organ functions, coronary angiography, fluorescence endoscopy, detection, imaging, and therapy of tumors, laser guided surgery, photoacoustic methods, and sonofluorescent methods.

Specific embodiments to accomplish some of the aforementioned biomedical applications are given below. The novel dyes of the present invention are prepared according to methods well known in the art and are illustrated in FIGS. 1–5.

Figure 1:
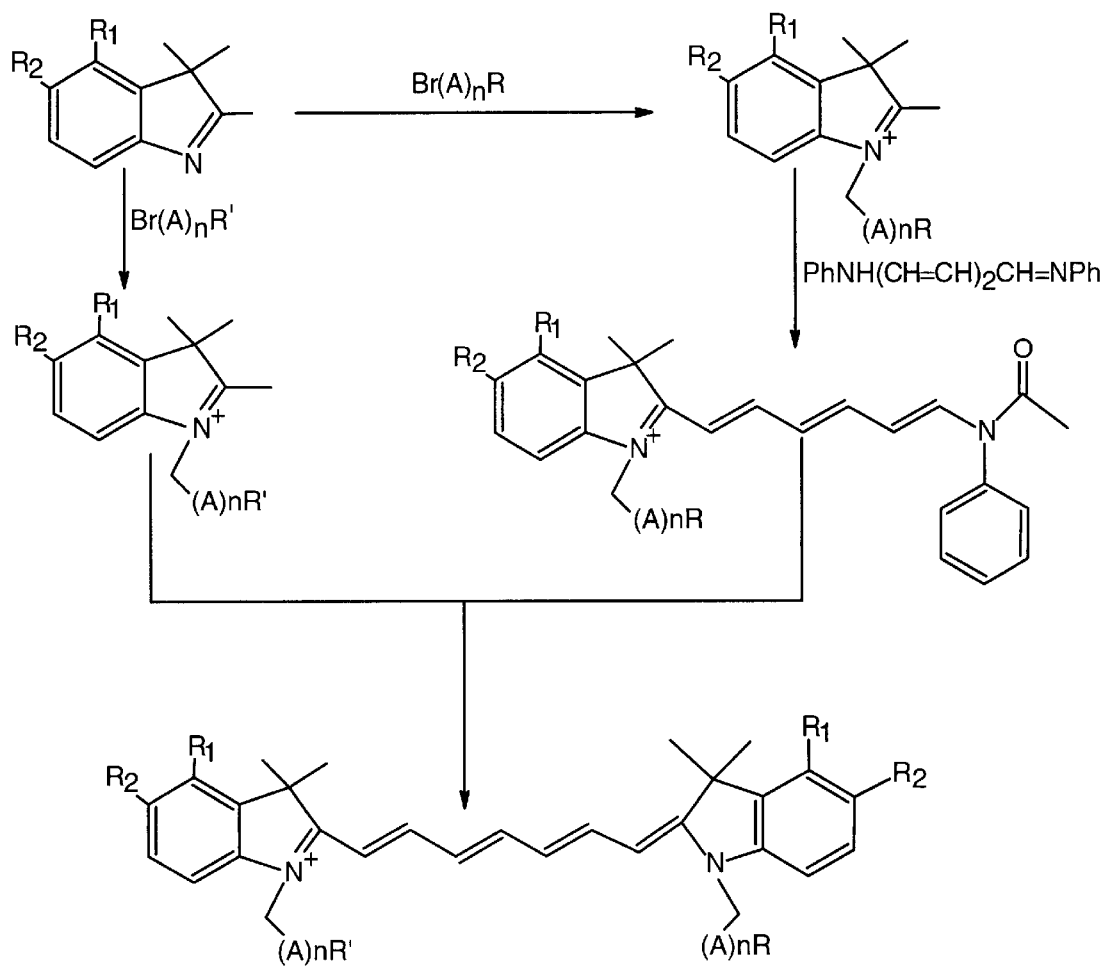
FIG. 1 shows the reaction pathway for the synthesis of bis-carboxylic acid cyanine dyes, wherein $A=CH_2$ or $CH_2OCH_2$; $R=COOH$; $R'=COOH$, NHFmoc; $CO_2t$-Bu; $SO_3^-$; $R_1=R_2=H$ (Formula 1) or $R_1$, $R_2$=fused phenyl (Formula 2).

FIG. 1 illustrates the synthetic scheme for bis-carboxylic acid cyanine dyes, where $A=CH_2$ or $CH_2OCH_2$; $R=COOH$; $R=COOH$, NHFmoc; $CO_2t$—Bu; $SO_3$; $R_1=R_2=H$ (Formula 1) or $R_1$, $R_2$=fused phenyl (Formula 2).

Figure 2:
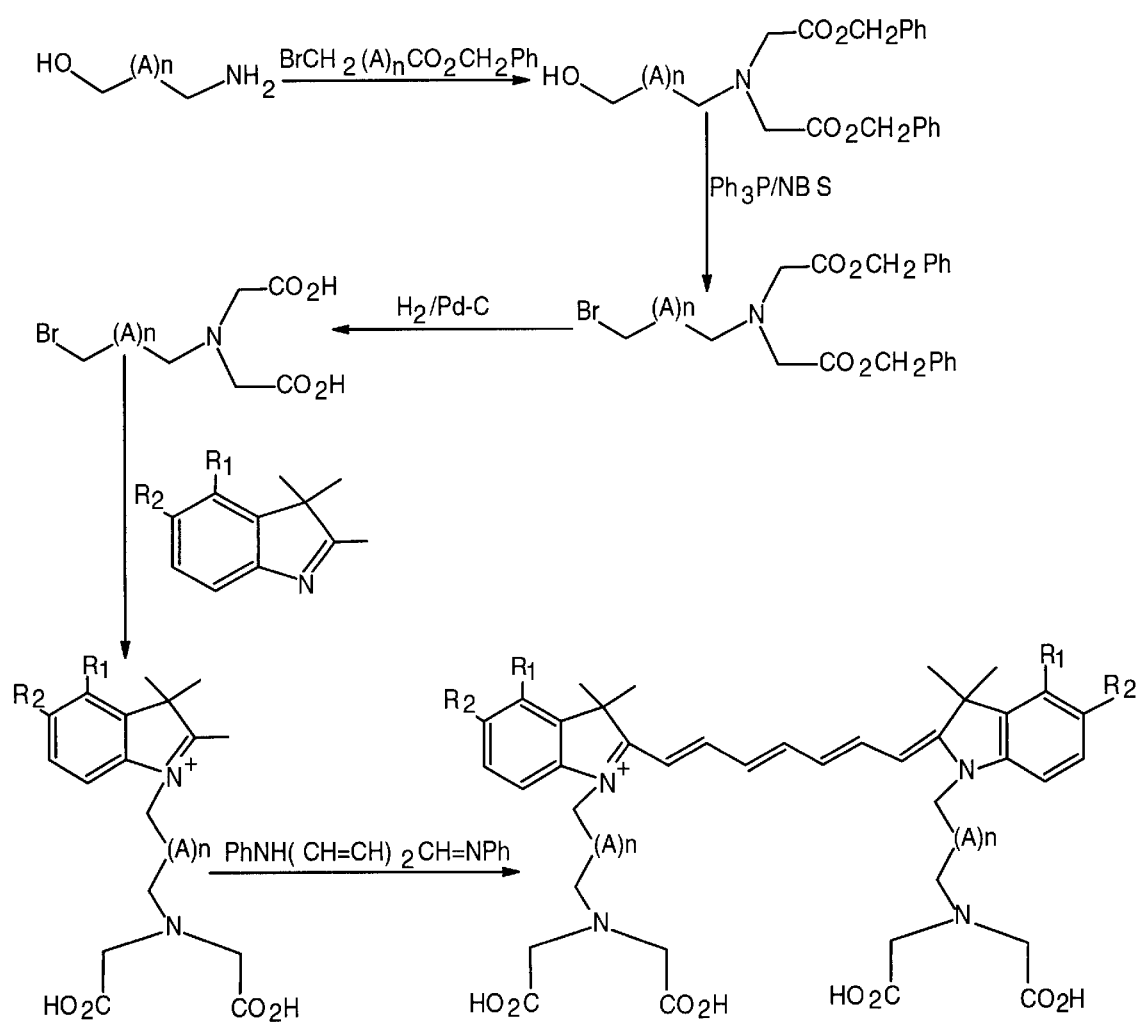
FIG. 2 shows the reaction pathway for the synthesis of tetracarboxylic acid cyanine dyes wherein $A=CH_2$ or $CH_2OCH_2$; $R_1=R_2=H$ (Formula 1) or $R_1$, $R_2$=fused phenyl (Formula 2).

FIG. 2 illustrates the synthetic scheme for tetracarboxylic acid cyanine dyes, where $A=CH_2$ or $CH_2OCH_2$; $R_1=R_2=H$ (Formula 1) or $R_1$, $R_2$=fused phenyl (Formula 2).

Figure 3:
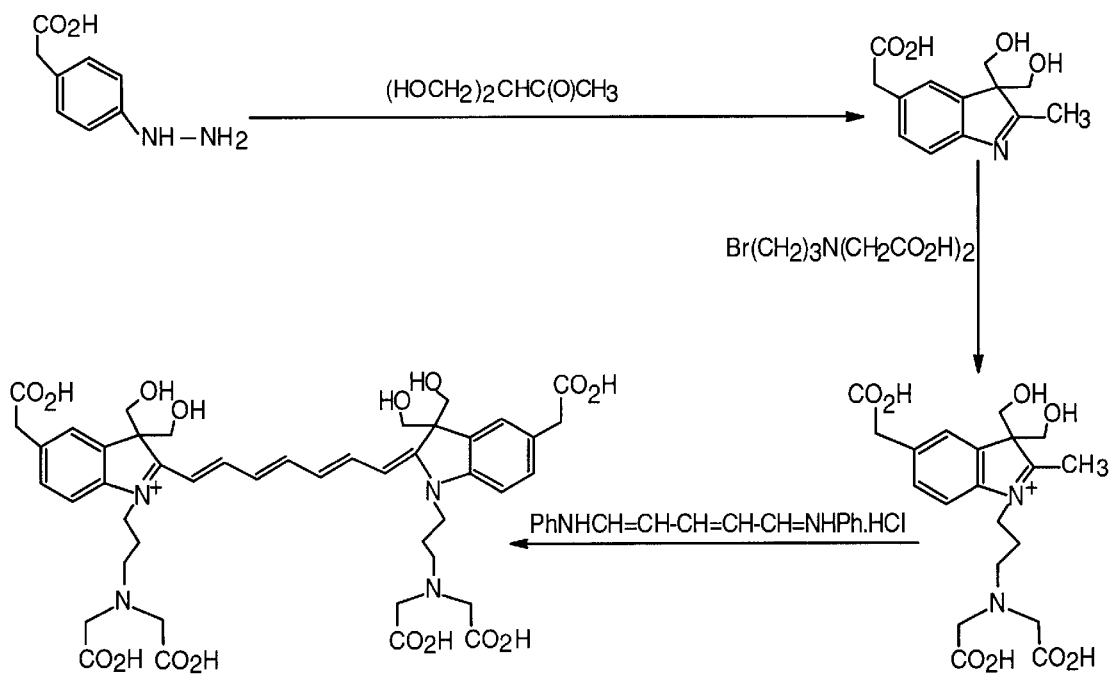
FIG. 3 shows the reaction pathway for the synthesis of polyhydroxycarboxylic acid cyanine dyes.

FIG. 3 illustrates the synthetic scheme for polyhydroxycarboxylic acid cyanine dyes.

Figure 4:
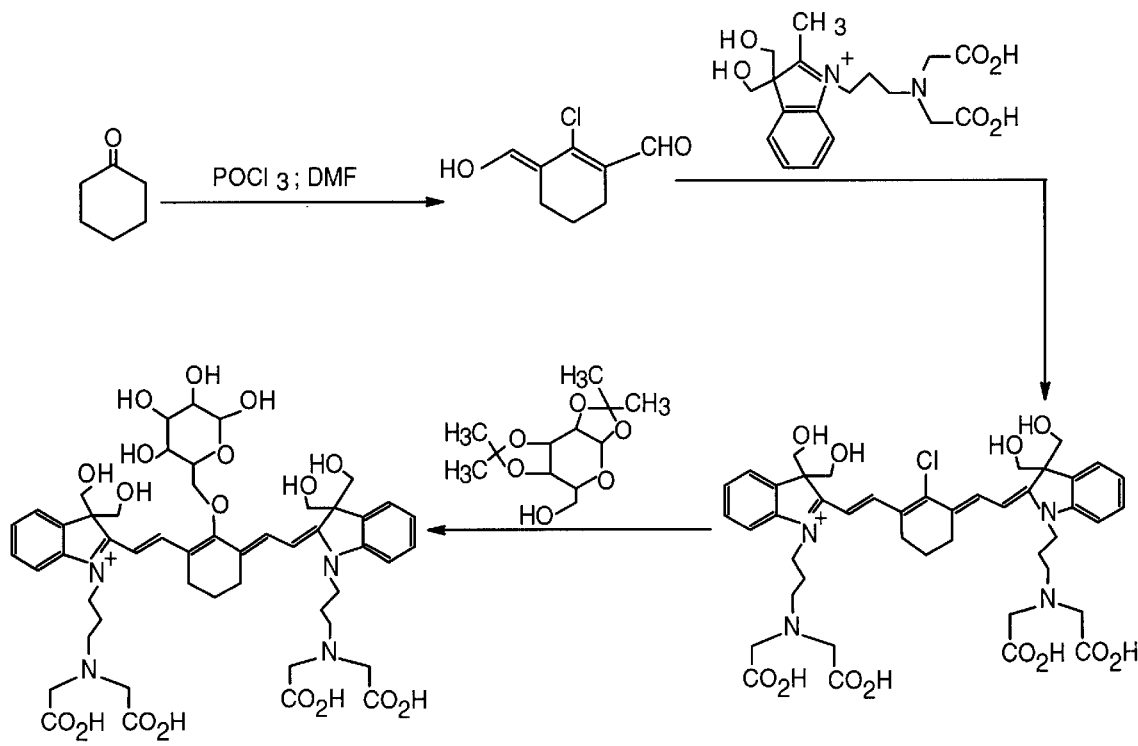
FIG. 4 shows the reaction pathway for the synthesis of non-aggregating cyanine dyes.

FIG. 4 illustrates the synthetic scheme for non-aggregating cyanine dyes.

Figure 5:
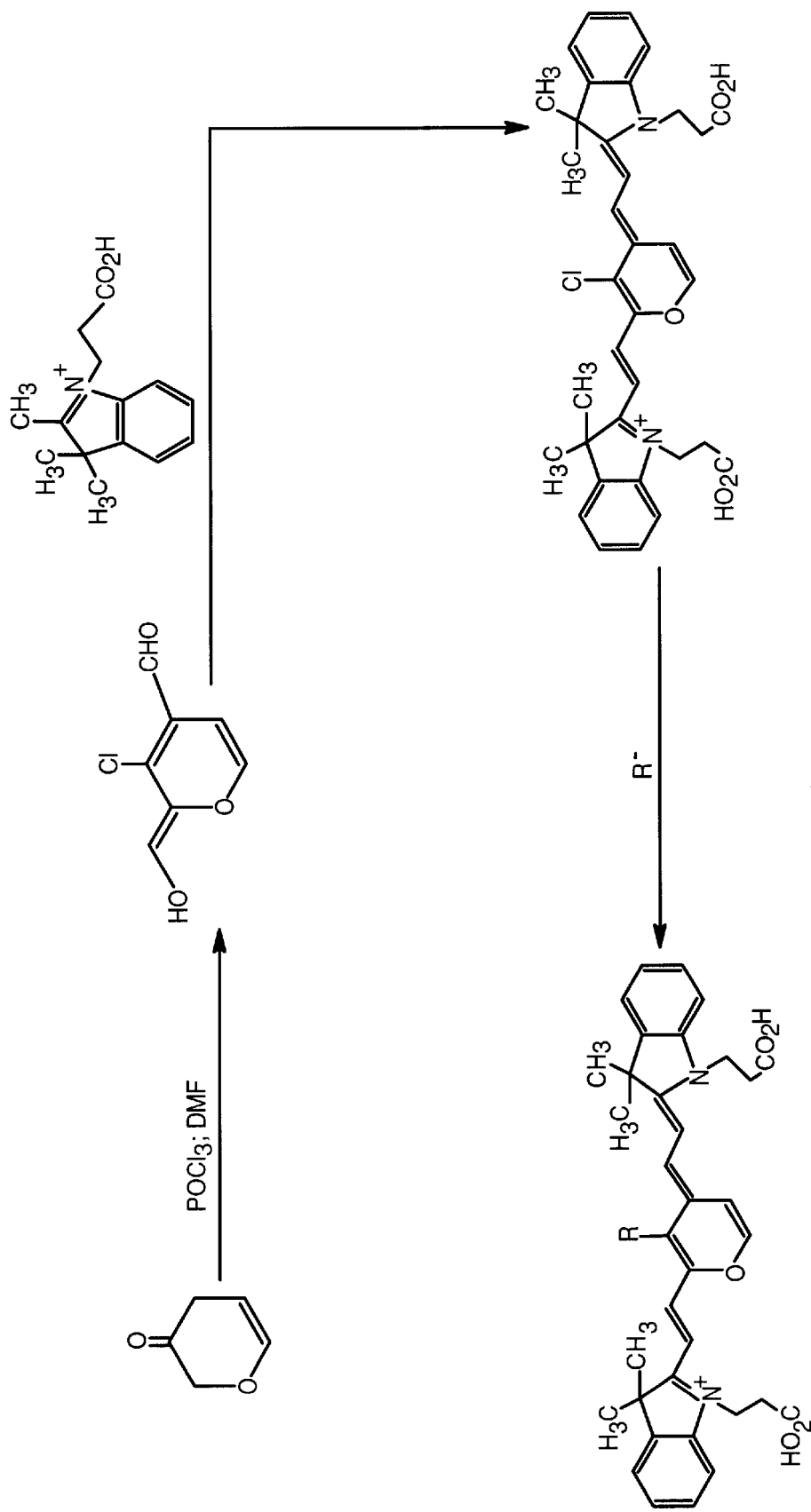
FIG. 5 shows the reaction pathway for the synthesis of long wavelength absorbing dyes.

FIG. 5 illustrates the synthetic scheme for long wavelength-absorbing tunable cyanine dyes.

In one embodiment, the inventive bioconjugates have the Formula 1 wherein $W^3$ and $X^3$ may be the same or different and are selected from the group consisting of —$C(CH_3)_2$, —$C((CH_2)OH)CH_3$, —$C((CH_2)_aOH)_2$, —$C((CH_2)_aCO_2H)CH_3$, —$C((CH_2)_aCO_2H)_2$, —$C((CH_2)_aNH_2)CH_3$, —$C((CH_2)_aNH_2)_2$, $C((CH_2)_aNR^3R^4)_2$, —$NR^3$, and —S—; $Y^3$ is selected from the group consisting of —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—$NR^3R^4$, and —$CH_2(CH_2OCH_2)_b$—$CH_2NR^3R^4$; $Z^3$ is selected from the group consisting of —$(CH_2)_a$—CONH—Dm, —$CH_2$—$(CH_2OCH_2)_b$—$CH_2$—CONH—Dm, —$(CH_2)_a$—NHCO—Dm, —$CH_2$—$(CH_2OCH_2)_b$—$CH_2$—NHCO—Dm, —$(CH_2)_a$—$NR^3R^4$, and —$CH_2(CH_2OCH_2)_b$—$CH_2NR^3R^4$; $A_1$ is a single or a double bond; $B_1$, $C_1$, and $D_1$ are independently selected from the group consisting of —O—, —S—, $NR^3$, $(CH_2)_a$—$CR^1R^2$, and —$CR^1$; $A_1$, $B_1$, $C_1$, and $D_1$ may together form a 6- to 10-membered carbocyclic ring or a 6- to 10-membered heterocyclic ring optionally containing one or more oxygen, nitrogen, or sulfur atom; $a_3$ and $b_3$ are independently from 0 to 3; $R^1$ to $R^4$, and $R^{29}$ to $R^{37}$ are independently selected from the group consisting of hydrogen, $C_1$–$C_{10}$ alkyl, $C_5$–$C_{12}$ aryl, $C_1$–$C_{10}$ alkoxyl, $C_1$–$C_{10}$ polyhydroxyalkyl, $C_5$–$C_{12}$ polyhydroxyaryl, $C_1$–$C_{10}$ aminoalkyl, mono- or oligosaccharide, peptide with 2 to 30 amino acid units, —$CH_2(CH_2OCH_2)_b$—$CH_2$—OH, —$(CH_2)_a$—$CO_2H$, —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—OH and —$CH_2$—$(CH_2OCH_2)_b$—$CO_2H$; Bm and Dm are independently selected from the group consisting of bioactive peptide containing 2 to 30 amino acid units, an antibody, a mono- or oligosaccharide, a glycopeptide, a metal chelating agent, a radioactive or nonradioactive metal complex, and an echogenic agent; a and c are independently from 1 to 10; and b and d are independently from 1 to 30.

In a second preferred embodiment, the inventive bioconjugates have the general Formula 2, wherein $W^4$ and $X^4$ may be the same or different and are selected from the group consisting of —$C(CH_3)_2$, —$C((CH_2)_aOH)CH_3$, —$C((CH_2)_a OH)_2$, —$C((CH_2)_aCO_2H)CH_3$, —$C((CH_2)_aCO_2H)_2$, —$C((CH_2)_aNH_2)CH_3$, —$C((CH_2)_aNH_2)_2$, —$C((CH_2)_a NR^3R^4)_2$, —$NR^3$, and —S—; $Y^4$ is selected from the group consisting of —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—$NR^3R^4$, and —$CH_2(CH_2OCH_2)_b$—$CH_2NR^3R^4$; $Z^4$ is selected from the group consisting of —$(CH_2)_a$—CONH—Dm, —$CH_2$—$(CH_2OCH_2)_b$—$CH_2$—CONH—Dm, —$(CH_2)_a$—NHCO—Dm, —$CH_2$—$(CH_2OCH_2)_b$—$CH_2$—NHCO—Dm, —$(CH_2)_a$—$NR^3R^4$, and —$CH_2$ $(CH_2OCH_2)_b$—$CH_2NR^3R^4$; $A_2$ is a single or a double bond; $B_2$, $C_2$, and $D_2$ are independently selected from the group consisting of —O—, —S—, $NR^3$, $(CH_2)_a$—$CR^1R^2$, and —$CR^1$; $A_2$, $B_2$, $C_2$, and $D_2$ may together form a 6- to 10-membered carbocyclic ring or a 6- to 10-membered heterocyclic ring optionally containing one or more oxygen, nitrogen, or sulfur atom; $a_4$ and $b_4$ are independently from 0 to 3; $R^1$ to $R^4$, and $R^{45}$ to $R^{57}$ are independently selected from the group consisting of hydrogen, $C_1$–$C_{10}$ alkyl, $C_5$–$C_{12}$ aryl, $C_1$–$C_{10}$ alkoxyl, $C_1$–$C_{10}$ polyhydroxyalkyl, $C_5$–$C_{12}$ polyhydroxyaryl, $C_1$–$C_{10}$ aminoalkyl, mono- or oligosaccharide, peptide with 2 to 30 amino acid units, —$CH_2(CH_2OCH_2)_b$—$CH_2$—OH, —$(CH_2)_a$—$CO_2H$, —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—OH and —$CH_2$—$(CH_2OCH_2)_b$—$CO_2H$; Bm and Dm are independently selected from the group consisting of a bioactive peptide containing 2 to 30 amino acid units, an antibody, a mono- or oligosaccharide, a glycopeptide, a metal chelating agent, a radioactive or nonradioactive metal complex, and an echogenic agent; a and c are independently from 1 to 10; and b and d independently from 1 to 30.

In a third embodiment, the inventive bioconjugates have the general Formula 3 wherein $W^5$ and $X^5$ may be the same or different and are selected from the group consisting of —$C(CH_3)_2$, —$C((CH_2)_aOH)CH_3$, —$C((CH_2)_aOH)_2$, —$C((CH_2)_aCO_2H)CH_3$, —$C((CH_2)_aCO_2H)_2$, —$C((CH_2)_a NH_2)CH_3$, —$C((CH_2)_aNH_2)_2$, —$C((CH_2)_aNR^3R^4)_2$, —$NR^3$, and —S—; $Y^5$ is selected from the group consisting of —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—$NR^3R^4$, and —$CH_2(CH_2OCH_2)_b$—$CH_2NR^3R^4$; $Z^5$ is selected from the group consisting of —$(CH_2)_a$—CONH—Dm, —$CH_2$—$(CH_2OCH_2)_b$—$CH_2$—CONH—Dm, —$(CH_2)_a$—NHCO—Dm, —$CH_2$—$(CH_2OCH_2)_b$—$CH_2$—NHCO—Dm, —$(CH_2)_a$—$NR^3R^4$, and —$CH_2(CH_2OCH_2)_b$—$CH_2NR^3R^4$; $A_3$ is a single or a double bond; $B_3$, $C_3$, and $D_3$ are independently selected from the group consisting of —O—, —S—, $NR^3$, $(CH_2)_a$—$CR^1R^2$, and —$CR^1$; $A_3$, $B_3$, $C_3$, and $D_3$ may together form a 6- to 10-membered carbocyclic ring or a 6- to 10-membered heterocyclic ring optionally containing one or more oxygen, nitrogen, or sulfur atom; $a_5$ is from 0 to 3; $R^1$ to $R^4$, and $R^{58}$ to $R^{66}$ are independently selected from the group consisting of hydrogen, $C_1$–$C_{10}$ alkyl, $C_5$–$C_{12}$ aryl, $C_1$–$C_{10}$ alkoxyl, $C_1$–$C_{10}$ polyhydroxyalkyl, $C_5$–$C_{12}$ polyhydroxy aryl, $C_1$–$C_{10}$ aminoalkyl, mono- or oligosaccharide, peptide with 2 to 30 amino acid units, —$CH_2(CH_2OCH_2)_b$—$CH_2$—OH, —$(CH_2)_a$—$CO_2H$, —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—OH and —$CH_2$—$(CH_2OCH_2)_b$—$CO_2H$; Bm and Dm are independently selected from the group consisting of a bioactive peptide containing 2 to 30 amino acid units, an antibody, a mono- or oligosaccharide, a glycopeptide, a metal chelating agent, a radioactive or nonradioactive metal complex, and an echogenic agent; a and c are independently from 1 to 10; and b and d are independently from 1 to 30.

In a fourth embodiment, the inventive bioconjugates have the general Formula 4 wherein $W^6$ and $X^6$ may be the same or different and are selected from the group consisting of —$C(CH_3)_2$, —$C((CH_2)_aOH)CH_3$, —$C((CH_2)_aOH)_2$, —$C((CH_2)_aCO_2H)CH_3$, —$C((CH_2)_aCO_2H)_2$, —$C((CH_2)_a NH_2)CH_3$, $C((CH_2)_aNH_2)_2$, —$C((CH_2)_aNR^3R^4)_2$, —$NR^3$, and —S—; $Y^6$ is selected from the group consisting of —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—$NR^3R^4$, and —$CH_2(CH_2OCH_2)_b$—$CH_2NR^3R^4$; $Z^6$ is selected from the group consisting of —$(CH_2)_a$—CONH—Dm, —$CH_2$—$(CH_2OCH_2)_b$—$CH_2$—CONH—Dm, —$(CH_2)_a$—NHCO—Dm, —$CH_2$—$(CH_2OCH_2)_b$—$CH_2$—NHCO—Dm, —$(CH_2)_a$—$NR^3R^4$, and —$CH_2(CH_2OCH_2)_b$—$CH_2NR^3R^4$; $A_4$ is a single or a double bond; $B_4$, $C_4$, and $D_4$ are independently selected from the group consisting of —O—, —S—, $NR^3$, $(CH_2)_a$—$CR^1R^2$, and —$CR^1$; $A_4$, $B_4$, $C_4$, and $D_4$ may together form a 6- to 10-membered carbocyclic ring or a 6- to 10-membered heterocyclic ring optionally containing one or more oxygen, nitrogen, or sulfur atom; $a_6$ is from 0 to 3; $R^1$ to $R^4$, and $R^{67}$ to $R^{79}$ are independently selected from the group consisting of hydrogen, $C_1$–$C_{10}$ alkyl, $C_5$–$C_{12}$ aryl, $C_1$–$C_{10}$ alkoxyl, $C_1$–$C_{10}$ polyhydroxyalkyl, $C_5$–$C_{12}$ polyhydroxy aryl, $C_1$–$C_{10}$ aminoalkyl, mono- or oligosaccharide, peptide with 2 to 30 amino acid units, —$CH_2(CH_2OCH_2)_b$—$CH_2$—OH, —$(CH_2)_a$—$CO_2H$, —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—OH and —$CH_2$—$(CH_2OCH_2)_b$—$CO_2H$; Bm and Dm are independently selected from the group consisting of a bioactive peptide containing 2 to 30 amino acid units, an antibody, a mono- or oligosaccharide, a glycopeptide, a metal chelating agent, a radioactive or nonradioactive metal complex, and an echogenic agent; a and c are independently from 1 to 10; and b and d are independently from 1 to 30.

Figure 6:
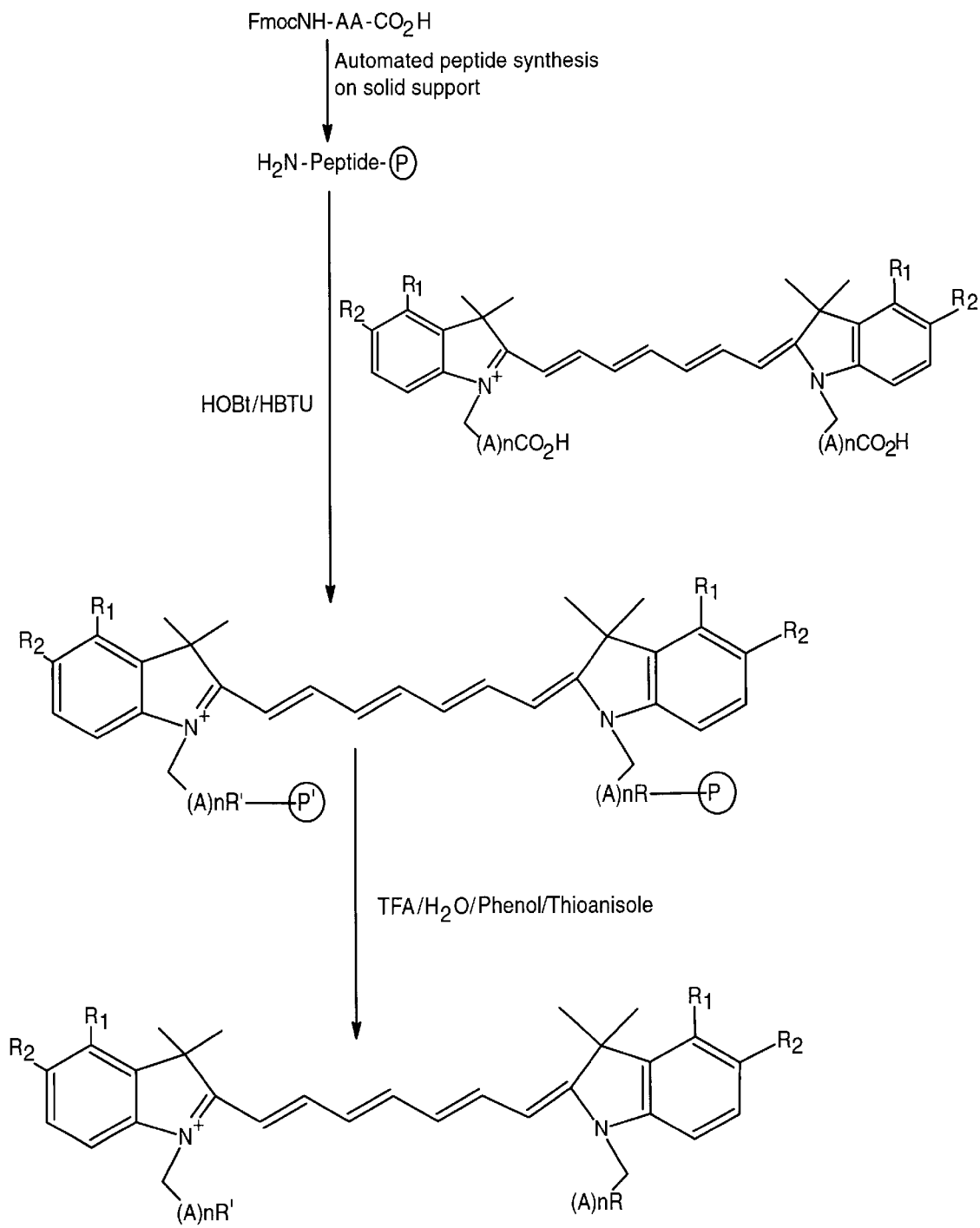
FIG. 6 shows the reaction pathway for the synthesis of cyanine dye bioconjugates wherein $A=CH_2$ or $CH_2OCH_2$; $R_1=R_2=H$ (Formula 1) or $R_1$, $R_2$=fused phenyl (Formula 2); AA=Amino Acids; R=CONH peptide; R'=R (Bis conjugate) or COOH (Mono conjugate); ⓟ=Solid support; (P')=Presence or absence depends on R' definition.

This invention is also related to the method of conjugating the inventive dyes to peptides or biomolecules by solid phase or solution synthesis methods. FIG. 6 illustrates the synthetic scheme for bioconjugates incorporating the cyanine dyes of FIGS. 1–5, using automated peptide synthesis in a solid support, where A=$CH_2$ or $CH_2OCH_2$; $R_1$=$R_2$=H (Formula 1) or $R_1$, $R_2$=fused phenyl (Formula 2); AA=amnio acids; R=CONH peptide; R'=R (bis conjugate) or COOH (mono conjugate); Ⓟ=solid support; Ⓟ'=presence or absence depends on R' definition.

This invention is also related to the method of preventing fluorescence quenching. It is known that cyanine dyes generally form aggregates in aqueous media, leading to fluorescence quenching. Where the presence of a hydrophobic core in the dyes leads to fluorescence quenching, the addition of a biocompatible organic solvent, such as 1–50% dimethylsulfoxide (DMSO) for example, restored fluorescence by preventing aggregation and allowed in vivo organ visualization.

The dye-biomolecule conjugates are used for optical tomographic, endoscopic, photoacoustic and sonofluorescent applications for the detection and treatment of tumors and other abnormalities.

Dye-biomolecule conjugates of the invention are also used for localized therapy. This may be accomplished by attaching a porphyrin or photodynamic therapy agent to a bioconjugate, shining light of appropriate wavelength for detection and treatment of the abnormality.

The inventive conjugates can also be used for the detection of the presence of tumors and other abnormalities by monitoring the blood clearance profile of the conjugates, for laser assisted guided surgery for the detection of small micrometastases of, e.g., somatostatin subtype 2 (SST-2) positive tumors, upon laparoscopy, and for diagnosis of atherosclerotic plaques and blood clots.

The compositions of the invention can be formulated into diagnostic and therapeutic compositions for enteral or parenteral administration. These compositions contain an effective amount of the dye along with conventional pharmaceutical carriers and excipients appropriate for the type of administration contemplated. For example, parenteral formulations advantageously contain the inventive agent in a sterile aqueous solution or suspension. Parenteral compositions may be injected directly or mixed with a large volume parenteral composition for systemic administration. Such solutions also may contain pharmaceutically acceptable buffers and, optionally, electrolytes such as sodium chloride.

Formulations for enteral administration may vary widely, as is well known in the art. In general, such formulations are liquids, which include an effective amount of the inventive agent in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement. Such doses may vary widely, depending upon the particular dye employed, the organs or tissues to be imaged, the imaging equipment being used, and the like. The diagnostic compositions of the invention are used in the conventional manner. The compositions may be administered to a patient, typically a warm-blooded animal, either systemically or locally to the organ or tissue to be imaged, and the patient then subjected to the imaging procedure.

The inventive compositions and methods represent an important approach to the synthesis and use of novel cyanine and indocyanine dyes with a variety of photophysical and chemical properties. The combination also represents an important approach to the use of small molecular targeting groups to image tumors by optical methods. The invention is further detailed in the following Examples, which are offered by way of illustration and are not intended to limit the scope of the invention in any manner.

EXAMPLE 1
Synthesis of Bis(ethylcarboxymethyl)indocyanine Dye
(FIG. 1, $R_1$, $R_2$=fused phenyl; $A=CH_2$, n=1 and $R=R'=CO_2H$)

A mixture of 1,1,2-trimethyl-[1H]-benz[e]indole (9.1 g, 43.58 mmoles) and 3-bromopropanoic acid (10.0 g, 65.37 mmoles) in 1,2-dichlorobenzene (40 mL) was heated at 110° C. for 12 hours. The solution was cooled to room temperature and the red residue obtained was filtered and washed with acetonitrile:diethyl ether (1:1) mixture. The solid obtained was dried under vacuum to give 10 g (64%) of light brown powder. A portion of this solid (6.0 g; 16.56 mmoles), glutaconaldehyde dianil monohydrochloride (2.36 g, 8.28 mmoles) and sodium acetate trihydrate (2.93 g, 21.53 mmoles) in ethanol (150 mL) were refluxed for 90 minutes. After evaporating the solvent, 40 mL of a 2 N aqueous HCl was added to the residue. The mixture was centrifuged and the supernatant was decanted. This procedure was repeated until the supernatant became nearly colorless. About 5 mL of water:acetonitrile (3:2) mixture was added to the solid residue and lyophilized to obtain 2 g of dark green flakes. The purity of the compound was established with $^1$H-NMR and liquid chromatography-mass spectroscopy (LC-MS)

EXAMPLE 2
Synthesis of Bis(pentylcarboxymethyl)indocyanine Dye
(FIG. 1, $R_1$, $R_2$=fused phenyl; $A=CH_2$, n=4 and $R=R'=CO_2H$)

A mixture of 1,1,2-trimethyl-[1H]-benz[e]indole (20 g, 95.6 mmoles) and 6-bromohexanoic acid (28.1 g, 144.1 mmoles) in 1,2-dichlorobenzene (250 mL) was heated at 110° C. for 12 hours. The green solution was cooled to room temperature and the brown solid precipitate formed was collected by filtration. After washing the solid with 1,2-dichlorobenzene and diethyl ether, the brown powder obtained (24 g, 64%) was dried under vacuum at room temperature. A portion of this solid (4.0 g; 9.8 mmoles), glutaconaldehyde dianil monohydrochloride (1.4 g, 5 mmoles) and sodium acetate trihydrate (1.8 g, 12.9 mmoles) in ethanol (80 mL) were refluxed for 1 hour. After evaporating the solvent, 20 mL of a 2 N aqueous HCl was added to the residue. The mixture was centrifuged and the supernatant was decanted. This procedure was repeated until the supernatant became nearly colorless. About 5 mL of water:acetonitrile (3:2) mixture was added to the solid residue and lyophilized to obtain about 2 g of dark green flakes. The purity of the compound was established with $^1$H-NMR and LC-MS.

EXAMPLE 3
Synthesis of Bisethylcarboxymethylindocyanine Dye
(FIG. 1, $R_1=R_2=H$; $A=CH_2$, n=1 and $R=R'=CO_2H$)

This compound was prepared as described in Example 1 except that 1,1,2-trimethylindole was used as the starting material.

EXAMPLE 4
Synthesis of Bis(hexaethyleneglycolcarboxymethyl) indocyanine Dye
(FIG. 1, $R_1=R_2$=fused phenyl; $A=CH_2OCH_2$, n=6 and $R=R'=CO_2H$)

This compound was prepared as described in Example 1 except that ω-bromohexaoxyethyleneglycolpropiolic acid was used in place of bromopropanoic acid and the reaction was carried out in 1,2-dimethoxypropane.

EXAMPLE 5
Synthesis of Bisethylcarboxymethylindocyanine Dye
(FIG. 2, $R_1=R_2$=fused phenyl; $A=CH_2$, and n=0)

A solution of 50 ml of dimethylformamide and benzyl bromoacetate (16.0 g, 70 mmol) was stirred in a 100-mL three-neck flask. Solid potassium bicarbonate (7.8 g, 78 mmol) was added. The flask was purged with argon and cooled to 0° C. with an ice bath. To the stirring mixture was added dropwise a solution of ethanolamine (1.9 g, 31 mmol) and 4 ml of dimethylformamide over 5 minutes. After the addition was complete the mixture was stirred for 1 hour at 0° C. The ice bath was removed and the mixture stirred at room temperature overnight. The reaction mixture was partitioned between 100 ml of methylene chloride and 100 ml of saturated sodium bicarbonate solution. The layers were separated and the methylene chloride layer was again washed with 100 ml of saturated sodium bicarbonate solution. The combined aqueous layers were extracted twice with 25 ml of methylene chloride. The combined methylene chloride layers were washed with 100 ml of brine, and dried over magnesium sulfate. The methylene chloride was removed with aspirator vacuum at about 35° C., and the remaining dimethylformamide was removed with vacuum at about 45° C. The crude material was left on a vacuum line overnight at room temperature.

The crude material was then dissolved in 100 ml of methylene chloride at room temperature. Triphenylphosphine (8.91 g, 34 mmol) was added and dissolved with stirring. An argon purge was started and the mixture was cooled to 0° C. with an ice bath. The N-bromosuccinimide (6.05 g, 34 mmol) was added portionwise over two minutes. The mixture was stirred for 1.5 hours at 0° C. The methylene chloride was removed with vacuum and gave purple oil. This oil was triturated with 200 ml of ether with constant manual stirring. During this time the oil became very thick. The ether solution was decanted and the oil was triturated with 100 ml of ether. The ether solution was decanted and the oil was again triturated with a 100 ml portion of ether. The ether was decanted and the combined ether solution was allowed to stand for about two hours to allow the triphenylphosphine oxide to crystallize. The ether solution was decanted from the crystals and the solid was washed with 100 ml of ether. The volume of the combined ether abstracts was reduced with vacuum until a volume of about 25 ml was obtained. This was allowed to stand over night at 0° C. Ether (10 ml) was added to the cold mixture, which was mixed to suspend the solid. The mixture was percolated through a column of 45 g of silica gel and eluted with ether, 75 ml fractions were collected. The fractions that contained product, as determined by thin layer chromatography, were pooled and the ether was removed with vacuum. This yielded 10.1 g of crude product. The material was flash chromatographed on silica gel with hexane, changing to 9:1 hexane:ether. The product-containing fractions were pooled and the solvents removed with vacuum. This yielded 7.4 g (57% yield) of pure product.

A mixture of 10% palladium on carbon (1 g) and a solution of the benzyl ester (10 g) in 150 ml of methanol was hydrogenolyzed at 25 psi for two hours. The mixture was filtered over celite and the residue was washed with methanol. The solvent was evaporated to give a viscous oil in quantitative yield.

Reaction of the bromide with 1,1,2-trimethyl-[1H]-benz[e]indole was carried out as described in Example 1.

EXAMPLE 6

Bis(ethylcarboxymethyldihydroxyl)indocyanine Dye (FIG. 3)

The hydroxy-indole compound is readily prepared by a known method (P. L. Southwick, et al., One pot Fischer synthesis of (2,3,3-trimethyl-3-H-indol-5-yl)-acetic acid derivatives as intermediates for fluorescent biolabels. *Org. Prep. Proced. Int. Briefs,* 1988, 20(3), 279–284). Reaction of p-carboxymethylphenylhydrazine hydrochloride (30 mmol, 1 equiv.) and 1,1-bis(hydroxymethyl)propanone (45 mmole, 1.5 equiv.) in acetic acid (50 mL) at room temperature for 30 minutes and at reflux for one minute gives (3,3-dihydroxymethyl-2-methyl-3-H-indol-5-yl)-acetic acid as a solid residue. The reaction of 3-bromopropyl-N,N-bis(carboxymethyl)amine, which was prepared as described in Example 5, with the intermediate indole and subsequent reaction of the indole intermediate with glutaconaldehyde dianil monohydrochloride (see Example 1) gives the desired product.

EXAMPLE 7

Synthesis of Bis(propylcarboxymethyl)indocyanine Dye (FIG. 4)

The intermediate 2-chloro-1-formyl-3-hydroxymethylenecyclohexane was prepared as described in the literature (G. A. Reynolds and K. H. Drexhage, Stable heptamethine pyrylium dyes that absorb in the infrared. *J. Org. Chem.,* 1977, 42(5), 885–888). Equal volumes (40 mL each) of dimethylformamide (DMF) and dichloromethane were mixed and the solution was cooled to –10° C. in acetone-dry ice bath. Under argon atmosphere, phosphorus oxychloride (40 mL) in dichloromethane was added dropwise to the cool DMF solution, followed by the addition of 10 g of cyclohexanone. The resulting solution was allowed to warm up to room temperature and refluxed for six hours. After cooling to room temperature, the mixture was poured into ice-cold water and stored at 4° C. for twelve hours. About 8 g of yellow powder was obtained after filtration. Condensation of the cyclic dialdehyde with the indole intermediate is carried out as described in Example 1. Further functionalization of the dye with bis isopropylidene acetal protected monosaccharide was accomplished by the method described in the literature (J. H. Flanagan, et al., Near infrared heavy-atom-modified fluorescent dyes for base-calling in DNA-sequencing application using temporal discrimination. *Anal. Chem.,* 1998, 70(13), 2676–2684).

EXAMPLE 8

Synthesis of Bis(ethylcarboxymethyl)indocyanine Dye (FIG. 5)

These dyes are prepared as described in Example 7. These dyes absorb in the infrared region. The typical example shown in FIG. 5 has an estimated absorption maximum at 1036 nm.

EXAMPLE 9

Synthesis of Peptides

The procedure described below is for the synthesis of Octreotate. The amino acid sequence of Octreotate is: D-Phe-Cys'-Tyr-D-Trp-Lys-Thr-Cys'-Thr (SEQ ID NO:1), wherein Cys' indicates the presence of an intramolecular disulfide bond between two cysteine amino acids. Other peptides of this invention were prepared by a similar procedure with slight modifications in some cases.

The octapeptide was prepared by an automated fluorenylmethoxycarbonyl (Fmoc) solid phase peptide synthesis using a commercial peptide synthesizer from Applied Biosystems (Model 432A SYNERGY Peptide Synthesizer). The first peptide cartridge contained Wang resin pre-loaded with Fmoc-Thr on 25-μmole scale. Subsequent cartridges contained Fmoc-protected amino acids with side chain protecting groups for the following amino acids: Cys(Acm), Thr (t-Bu), Lys(Boc), Trp(Boc) and Tyr(t-Bu). The amino acid cartridges were placed on the peptide synthesizer and the product was synthesized from the C- to the N-terminal position. The coupling reaction was carried out with 75 μmoles of the protected amino acids in the presence of 2-(1H-benzotriazol-1-yl)-1,1,3,3-tetramethyluronium hexafluorophosphate (HBTU)/N-hydroxybenzotriazole (HOBt). The Fmoc protecting group was removed with 20% piperidine in dimethylformamide. After the synthesis was complete, the thiol group was cyclized with thallium trifluoroacetate and the product was cleaved from the solid support with a cleavage mixture containing trifluoroacetic acid (85%):water (5%):phenol (5%):thioanisole (5%) for 6 hours. The peptide was precipitated with t-butyl methyl ether and lyophilized with water:acetonitrile (2:3) mixture. The peptide was purified by HPLC and analyzed with LC/MS.

Octreotide, D-Phe-Cys'-Tyr-D-Trp-Lys-Thr-Cys'-Thr-OH (SEQ ID NO:2), wherein Cys' indicates the presence of an intramolecular disulfide bond between two cysteine amino acids, was prepared by the same procedure.

Bombesin analogs were prepared by the same procedure except that cyclization with thallium trifluoroacetate was not needed. Side-chain deprotection and cleavage from the resin was carried out with 50 µL each of ethanedithiol, thioanisole and water, and 850 µL of trifluoroacetic acid. Two analogues were prepared: Gly-Ser-Gly-Gln-Trp-Ala-Val-Gly-His-Leu-Met-$NH_2$ (SEQ ID NO:3) and Gly-Asp-Gly-Gln-Trp-Ala-Val-Gly-His-Leu-Met-$NH_2$ (SEQ ID NO:4).

Cholecystokinin octapeptide analogs were prepared as described for Octreotate without the cyclization step. Three analogs were prepared: Asp-Tyr-Met-Gly-Trp-Met-Asp-Phe-$NH_2$ (SEQ ID NO:5); Asp-Tyr-Nle-Gly-Trp-Nle-Asp-Phe-$NH_2$ (SEQ ID NO:6); and D-Asp-Tyr-Nle-Gly-Trp-Nle-Asp-Phe-$NH_2$ (SEQ ID NO:7) wherein Nle is norleucine.

A neurotensin analog, D-Lys-Pro-Arg-Arg-Pro-Tyr-Ile-Leu (SEQ ID NO:8), was prepared as described for Octreotate without the cyclization step.

EXAMPLE 10
Synthesis of Peptide-dye Conjugates (FIG. 6)

The method described below is for the synthesis of Octreotate-cyanine dye conjugates, but a similar procedure is used for the synthesis of other peptide-dye conjugates.

Octreotate was prepared as described in Example 9 but the peptide was not cleaved from the solid support and the N-terminal Fmoc group of Phe was retained. The thiol group was cyclized with thallium trifluoroacetate and the Phe was deprotected to liberate the free amine. Bisethylcarboxymethylindocyanine dye (53 mg, 75 µmoles) was added to an activation reagent consisting of a 0.2 M solution of HBTU/HOBt in DMSO (375 µL), and 0.2 M solution of diisopropylethylamine in DMSO (375 µL). The activation was complete in about 30 minutes and the resin-bound peptide (25 µmoles) was added to the dye. The coupling reaction was carried out at room temperature for three hours. The mixture was filtered and the solid residue was washed with DMF, acetonitrile and THF. After drying the green residue, the peptide was cleaved from the resin and the side chain protecting groups were removed with a mixture of 85% trifluoroacetic acid, 2.5% water, 2.5% thioanisole and 2.5% phenol. The resin was filtered and cold t-butyl methyl ether (MTBE) was used to precipitate the dye-peptide conjugate, which was dissolved in acetonitrile:water (2:3) mixture and lyophilized. The product was purified by HPLC to give the monoOctreotate-Bisethylcarboxymethylindocyanine dye (Cytate 1, 80%) and the bisOctreotate-Bisethylcarboxymethylindocyanine dye (Cytate 2, 20%). The monoOctreotate conjugate is obtained almost exclusively (>95%) over the bis conjugate by reducing the reaction time to two hours. However, this also leads to incomplete reaction, and the free Octreotate must be carefully separated from the dye conjugate in order to avoid saturation of the receptors by the non-dye conjugated peptide.

Octreotate-bispentylcarboxymethylindocyanine dye was prepared as described above with some modifications. Bispentylcarboxymethylindocyanine dye (60 mg, 75 µmoles) was added to an activation reagent consisting of a 0.2 M solution of HBTU/HOBt in DMSO (400 µL), and 0.2 M solution of diisopropylethylamine in DMSO (400 µL). The activation was complete in about 30 minutes and the resin-bound peptide (25 µmoles) was added to the dye. The reaction was carried out at room temperature for three hours. The mixture was filtered and the solid residue was washed with DMF, acetonitrile and THF. After drying the green residue, the peptide was cleaved from the resin and the side chain protecting groups were removed with a mixture of 85% trifluoroacetic acid, 2.5% water, 2.5% thioanisole and 2.5% phenol. The resin was filtered and cold t-butyl methyl ether (MTBE) was used to precipitate the dye-peptide conjugate, which was dissolved in an acetonitrile:water (2:3) mixture and lyophilized. The product was purified by HPLC to give Octreotate-1,1,2-trimethyl-[1H]-benz[e]indole propanoic acid conjugate (10%), monoOctreotate-bispentylcarboxymethylindocyanine dye (Cytate 3, 60%) and bisOctreotate-bispentylcarboxymethylindocyanine dye (Cytate 4, 30%).

EXAMPLE 11
Formulation of Peptide-dye Conjugates in Dimethyl Sulfoxide (DMSO)

The dye-peptide conjugates are sparingly soluble in water and require the addition of solubilizing agents or co-solvents. Addition of 1–20% aqueous ethanol to the conjugates partially quenched the fluorescence intensity in vitro and the fluorescence was completely quenched in vivo (the conjugate was not detected by the charged coupled device (CCD) camera). Addition of 1–50% of DMSO either re-established or increased the fluorescence intensity of the conjugates in vitro and in vivo. The dye fluorescence remained intense for over one week. The DMSO formulations were well tolerated by experimental animals used for this invention.

EXAMPLE 12
Imaging of Pancreatic Ductal Adenocarcinoma (DSL 6A) with Indocyanine Green (ICG)

A non-invasive in vivo fluorescence imaging apparatus was employed to assess the efficacy of contrast agents developed for tumor detection in animal models. A LaserMax Inc. laser diode of nominal wavelength 780 nm and nominal power of 40 mW was used. The detector was a Princeton Instruments model RTE/CCD-1317-K/2 CCD camera with a Rodenstock 10 mm F2 lens (stock #542.032.002.20) attached. An 830 nm interference lens (CVI Laser Corp., part # F10-830-4-2) was mounted in front of the CCD input lens such that only emitted fluorescent light from the contrast agent was imaged. Typically, an image of the animal was taken pre-injection of contrast agent. This image was subsequently subtracted (pixel by pixel) from the post injection images. However, the background subtraction was never done once the animal had been removed from the sample area and returned at a later time for images taken several hours post injection.

DSL 6A tumors were induced in male Lewis rats in the left flank area by the introduction of material from a solid (donor) implant and the tumors were palpable in approximately 14 days. The animals were anesthetized with xylazine; ketamine; acepromazine 1.5:1.5:0.5 at 0.8 mL/kg via intramuscular injection. The area of the tumor (left flank) was shaved to expose tumor and surrounding surface area. A 21 gauge butterfly equipped with a stopcock and two syringes containing heparinized saline was placed into the later tail vein of the rat. Patency of the vein was checked prior to administration of the ICG via the butterfly apparatus. Each animal received 500 mL of a 0.42 mg/mL solution of ICG in water.

Figure 7A:
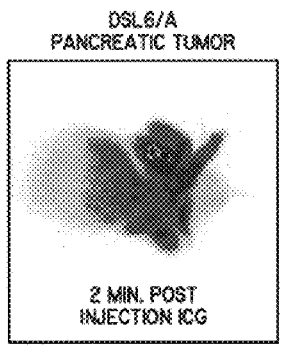
FIGS. 7A–F represent images at 2 minutes and 30 minutes post injection of indocyanine green (ICG) into rats with various tumors.
Figure 7C:
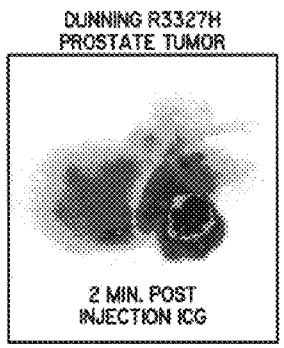
Figure 7E:
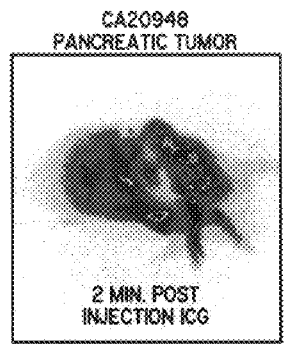
Figure 7B:
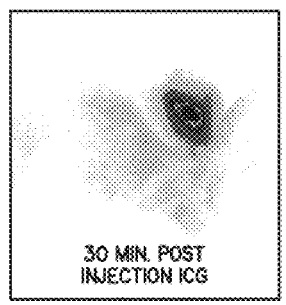

FIGS. 7A–B are tumor images of two minutes (FIG. 7A) and 30 minutes (FIG. 7B) post bolus injection of a 0.5 ml aqueous solution of ICG (5.4 µm). Tetracarboxylic acid cyanine dyes were synthesized as shown in FIG. 2, with A=$CH_2$ or $CH_2OCH_2$; $R_1$=$R_2$=H (Formula 1) or $R_1$, $R_2$=fused phenyl (Formula 2).

The Figures are false color images of fluorescent intensity measured at the indicated times, with images constrained to the tumor and a small surrounding area. As is shown, the dye intensity in the tumor is considerably diminished 30 minutes post-ICG injection.

EXAMPLE 13
Imaging of Prostatic Carcinoma (R3327-H) with Indocyanine Green (ICG)

Figure 7D:
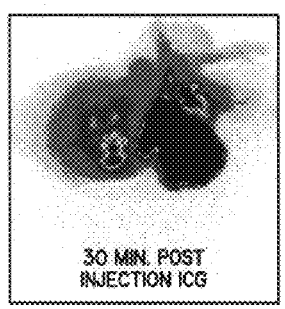

The imaging apparatus and the procedure used are described as in Example 12. Prostrate tumors (Dunning R3327-H) were induced in young male Copenhagen rats in the left flank area from a solid implant. These tumors grow very slowly and palpable masses were present 4–5 months post implant. FIGS. 7C–D are images of a rat with an induced prostatic carcinoma tumor (R3327-H) imaged at two minutes (FIG. 7C) and minutes (FIG. 7D) post injection.

The Figures are false color images of fluorescent intensity measured at the indicated times, with images constrained to the tumor and a small surrounding area. As is shown, the dye intensity in the tumor is considerably diminished 30 minutes post-ICG injection.

EXAMPLE 14
Imaging of Rat Pancreatic Acinar Carcinoma (CA20948) with Indocyanine Green (ICG)

Figure 7F:
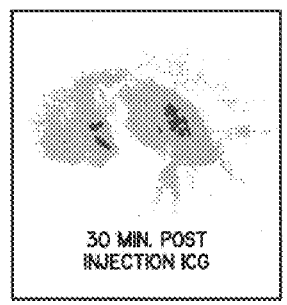

The imaging apparatus and the procedure used are described in Example 12. Rat pancreatic acinar carcinoma expressing the SST-2 receptor (CA20948) was induced by solid implant technique in the left flank area, and palpable masses were detected nine days post implant. The images obtained at 2 and 30 minutes post injection are shown in FIGS. 7E–F. FIGS. 7E–F are images of a rat with an induced pancreatic acinar carcinoma (CA20948) expressing the SST-2 receptor imaged at two minutes (FIG. 7E) and 30 minutes (FIG. 7F) post injection.

The Figures are false color images of fluorescent intensity measured at the indicated times, with images constrained to the tumor and a small surrounding area. As is shown, the dye intensity in the tumor is considerably diminished and almost absent 30 minutes post-ICG injection.

EXAMPLE 15
Imaging of Rat Pancreatic Acinar Carcinoma (CA20948) with Cytate 1

The imaging apparatus and the procedure used are described in Example 12 except that each animal received 500 µl of a 1.0 mg/mL solution of Cytate 1 solution of 25% dimethylsulfoxide in water.

Rat pancreatic acinar carcinoma expressing the SST-2 receptor (CA20948) were induced by solid implant technique in the left flank area, and palpable masses were detected 24 days post implant. Images were obtained at various times post injection. Uptake into the tumor was seen at two minutes but was not maximal until about five minutes.

Figure 8A:
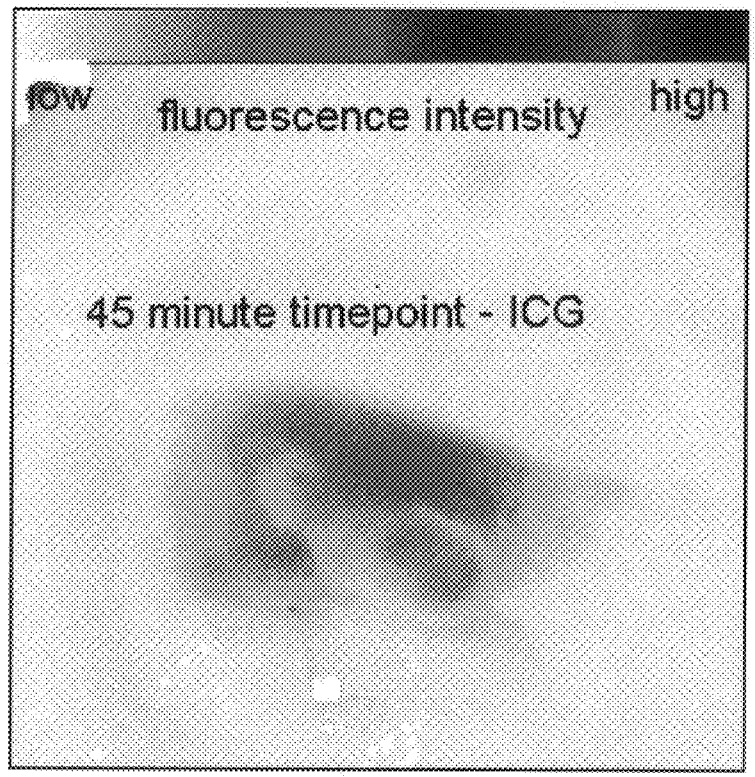
FIGS. 8A–B show a comparison of the uptake of ICG (FIG. 8A) and Cytate 1 (FIG. 8B) in rats with the pancreatic acinar carcinoma (CA20948).
Figure 8B:
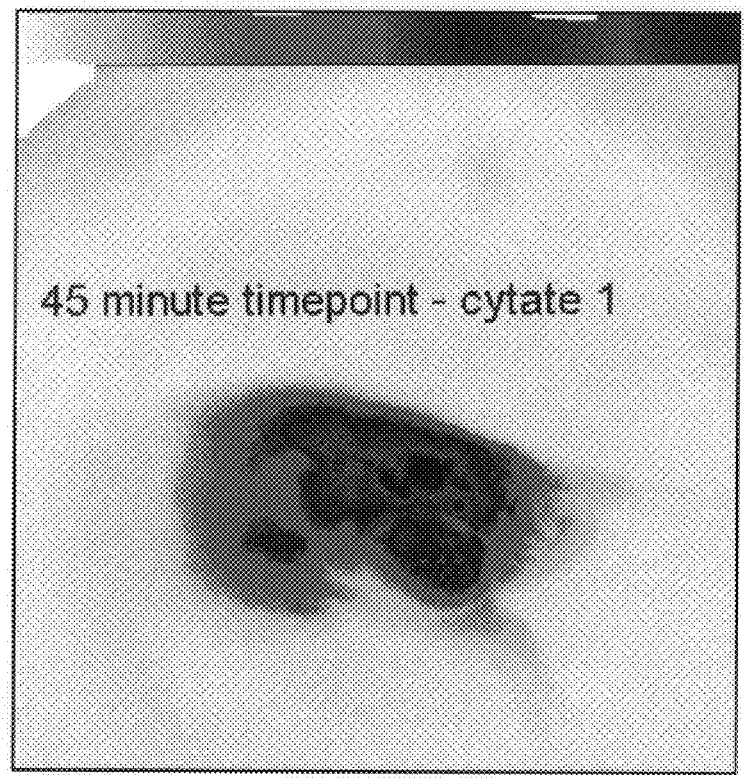

FIGS. 8A–B show a comparison of the uptake of ICG and Cytate 1 at 45 minutes in rats with the CA20948 tumor cell line. By 45 minutes the ICG has mostly cleared (FIG. 8A) whereas the Cytate 1 is still quite intense (FIG. 8B). This dye fluorescence remained intense in the tumor for several hours post-injection.

EXAMPLE 16
Imaging of Rat Pancreatic Acinar Carcinoma(CA20948) with Cytate 1 Compared with Imaging with Indocyanine Green Using indocyanine green (ICG), three different tumor lines were imaged optically using a CCD camera apparatus. Two of the lines, DSL 6/A (pancreatic) and Dunning R3327H (prostate) indicated slow perfusion of the agent over time into the tumor and reasonable images were obtained for each. The third line, CA20948 (pancreatic), indicated only a slight but transient perfusion that was absent after only 30 minutes post injection. This indicated no non-specific localization of ICG into this line compared to the other two tumor lines, suggesting a different vascular architecture for this type of tumor (see FIGS. 7A–F). The first two tumor lines (DSL 6/A and R3327H) are not as highly vascularized as CA20948 which is also rich in somatostatin (SST-2) receptors. Consequently, the detection and retention of a dye in this tumor model is a good index of receptor-mediated specificity.

Figure 9A:
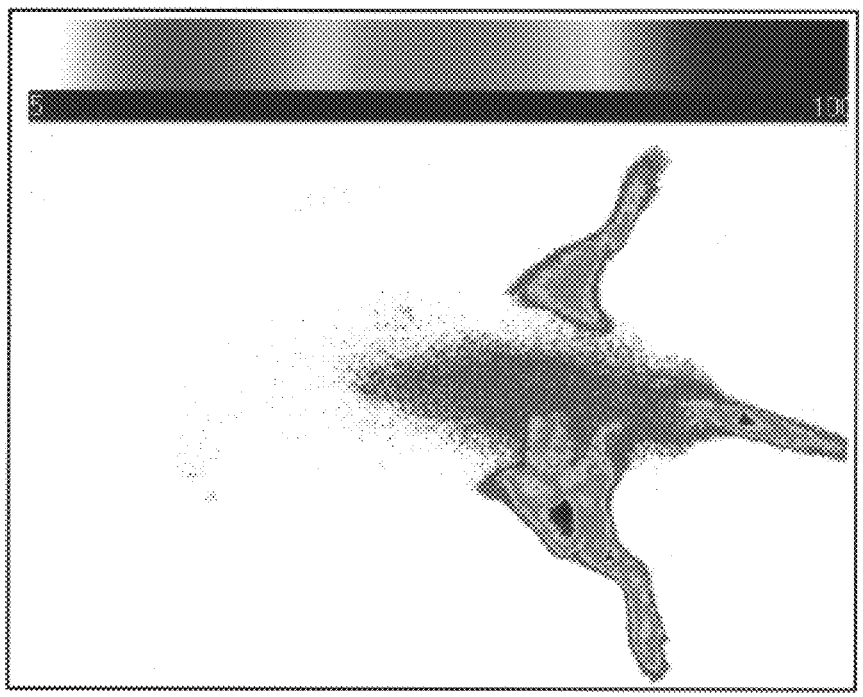
FIGS. 9A–B show images of rats with the pancreatic acinar carcinoma (CA20948) 45 minutes (FIG. 9A) and 27 hours (FIG. 9B) post injection of Cytate 1.
Figure 9B:
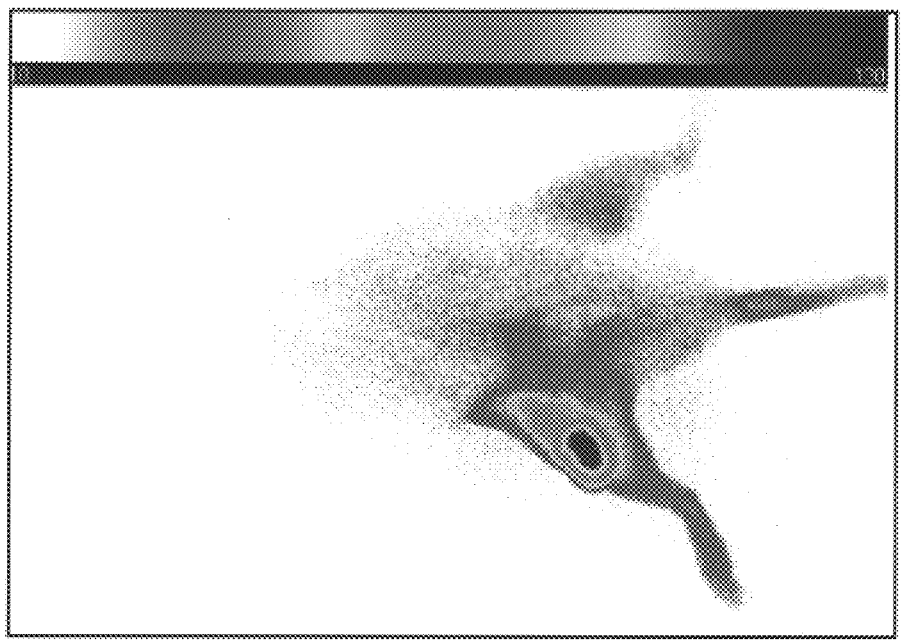

Octreotate is known to target somatostatin (SST-2) receptors, hence, cyano-Octreotates (Cytate 1 and Cytate 2) was prepared. Cytate 1 was evaluated in the CA20948 Lewis rat model. Using the CCD camera apparatus, localization of this dye was observed in the tumor (indicated by arrow) at 45 minutes post injection (FIG. 9A). At 27 hours post injection, the animal was again imaged (FIG. 9B). Tumor visualization was easily observed (indicated by arrow) showing specificity of this agent for the SST-2 receptors present in the CA20948 tumor line.

Figure 10:
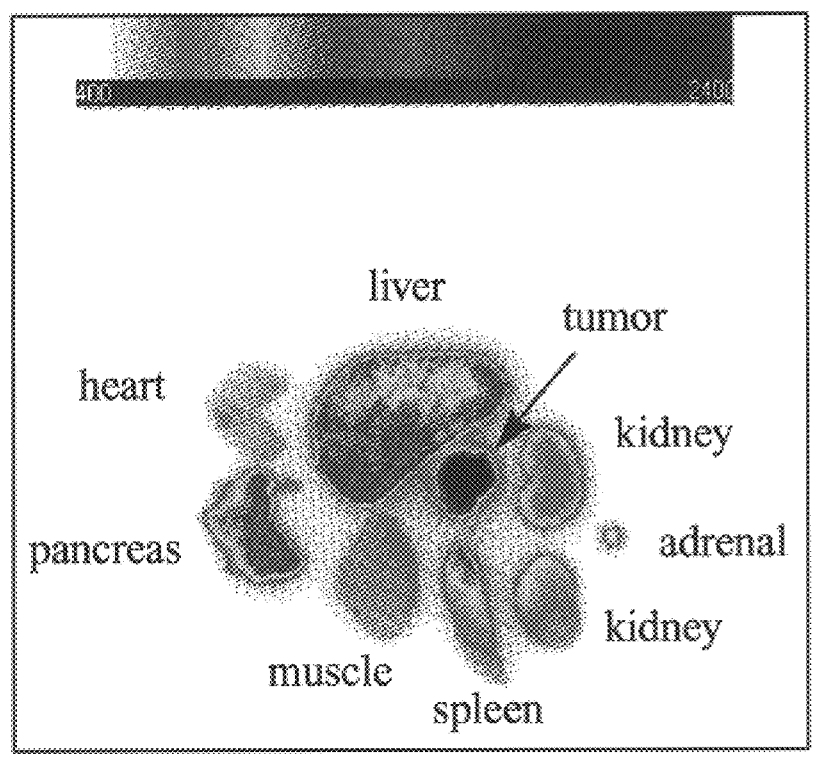
FIG. 10 is an image of individual organs taken from a rat with pancreatic acinar carcinoma (CA20948) about 24 hours after injection with Cytate 1.

Individual organs were removed at about 24 hours post Cytate 1 administration and imaged. As shown in FIG. 10, high uptake of Cytate 1 was observed in the pancreas, adrenals and tumor tissue, while heart, muscle, spleen and liver indicated significantly lower uptake. These data correlate well with radiolabeled Octreotate in the same model system (M. de Jong, et al. *Cancer Res.* 1998, 58, 437–441).

EXAMPLE 17
Imaging of Rat Pancreatic Acinar Carcinoma (AR42-J) with Bombesinate The AR42-J cell line is derived from exocrine rat pancreatic acinar carcinoma. It can be grown in continuous culture or maintained in vivo in athymic nude mice, SCID mice, or in Lewis rats. This cell line is particularly attractive for in vitro receptor assays, as it is known to express a variety of hormone receptors including cholecystokinin (CCK), epidermal growth factor (EGF), pituitary adenylate cyclase activating peptide (PACAP), somatostatin (SST-2) and bombesin.

In this model, male Lewis rats were implanted with solid tumor material in a similar manner as described for the CA20948 rat model. Palpable masses were present seven days post implant, and imaging studies were conducted on animals at 10–12 days post implant when the mass had achieved about 2–2.5 g.

Figure 11:
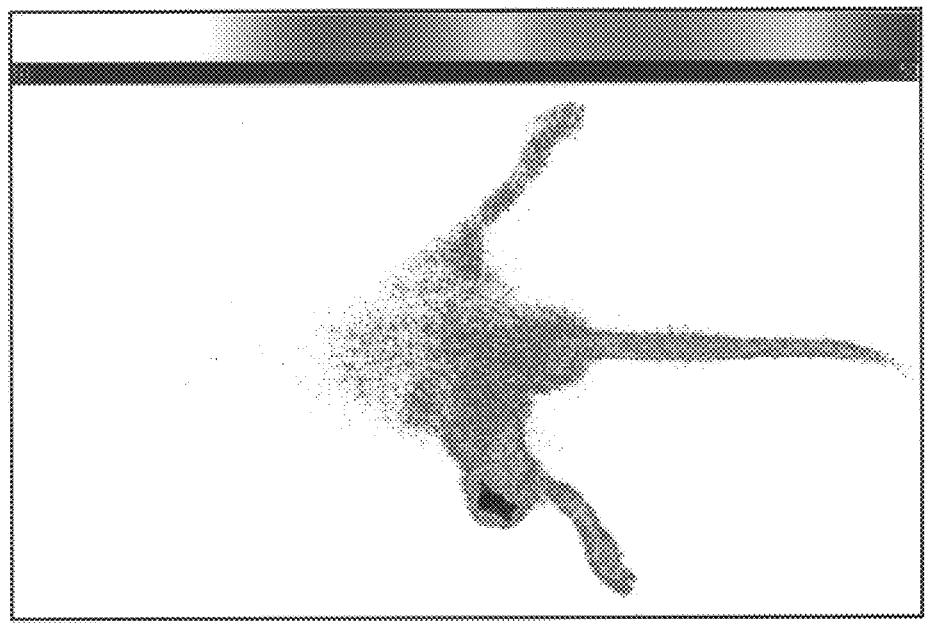
FIG. 11 is an image of bombesinate in an AR42-J tumor-bearing rat 22 hours after injection.

FIG. 11 is an image of bombesinate in an AR42-J tumor-bearing rat, as described in Example 16, at 22 hours post injection of bombesinate. As shown in FIG. 11, specific localization of the bioconjugate in the tumor (indicated by arrow) was observed.

EXAMPLE 18
Monitoring of the Blood Clearance Profile of Peptide-Dye Conjugates A laser of appropriate wavelength for excitation of the dye chromophore was directed into one end of a fiber optic bundle and the other end was positioned a few millimeters from the ear of a rat. A second fiber optic bundle was also positioned near the same ear to detect the emitted fluorescent light and the other end was directed into the optics and electronics for data collection. An interference filter (IF) in the collection optics train was used to select emitted fluorescent light of the appropriate wavelength for the dye chromophore.

Sprague-Dawley or Fischer 344 rats were used in these studies. The animals were anesthetized with urethane administered via intraperitoneal injection at a dose of 1.35 g/kg body weight. After the animals had achieved the desired plane of anesthesia, a 21 gauge butterfly with 12" tubing was placed in the lateral tail vein of each animal and flushed with heparinized saline. The animals were placed onto a heating pad and kept warm throughout the entire study. The lobe of the left ear was affixed to a glass microscope slide to reduce movement and vibration.

Incident laser light delivered from the fiber optic was centered on the affixed ear. Data acquisition was then initiated, and a background reading of fluorescence was obtained prior to administration of the test agent. For Cytates 1 or 2, the peptide-dye conjugate was administered to the animal through a bolus injection, typically 0.5 to 2.0 ml, in the lateral tail vein. This procedure was repeated with several dye-peptide conjugates in normal and tumor bearing rats. Representative profiles as a method to monitor blood clearance of the peptide-dye conjugate in normal and tumor bearing animals are shown in FIGS. 12–16. The data were analyzed using a standard sigma plot software program for a one compartment model.

Figure 12:
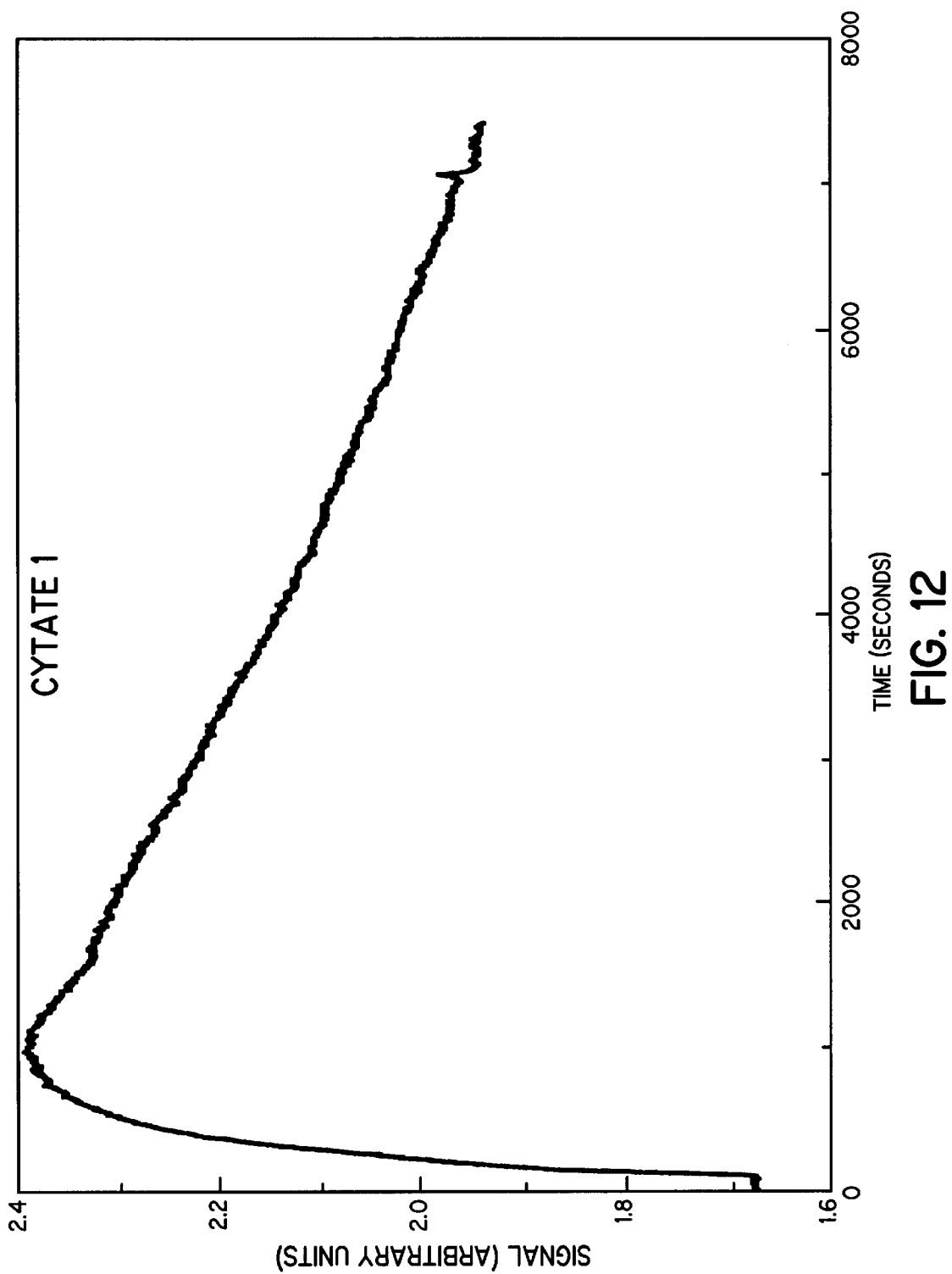
FIG. 12 is the clearance profile of Cytate 1 from the blood of a normal rat.
Figure 13:
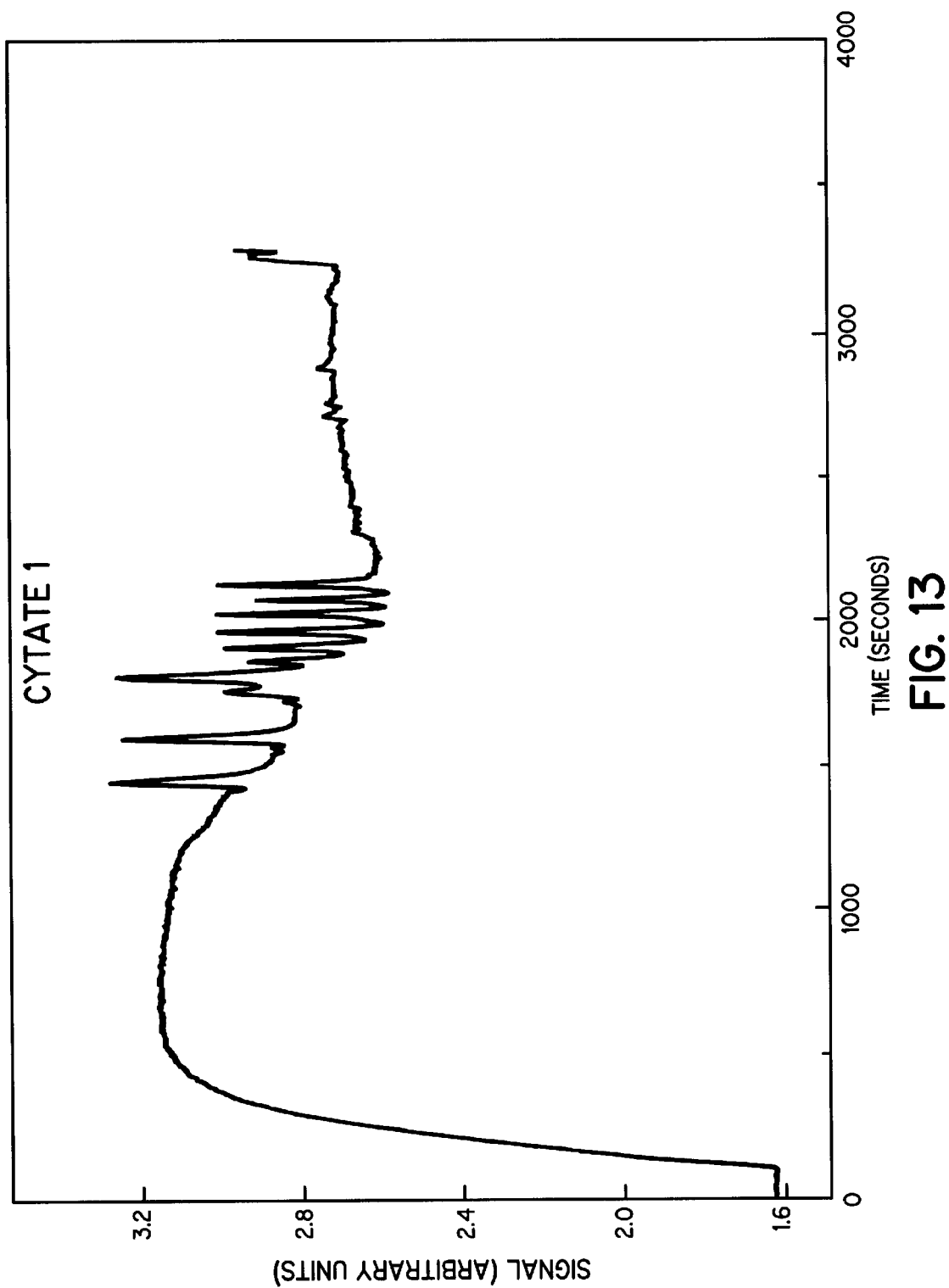
FIG. 13 is the clearance profile of Cytate 1 from the blood of a pancreatic tumor-bearing rat.

In rats treated with Cytates 1 or 2, the fluorescence signal rapidly increased to a peak value. The signal then decayed as a function of time as the conjugate cleared from the blood stream. FIG. 12 shows the clearance profile of Cytate 1 from the blood of a normal rat monitored at 830 nm after excitation at 780 nm. FIG. 13 shows the clearance profile of Cytate 1 from the blood of a pancreatic tumor (CA20948)-bearing rat also monitored an 830 nm after excitation at 780 nm.

Figure 14:
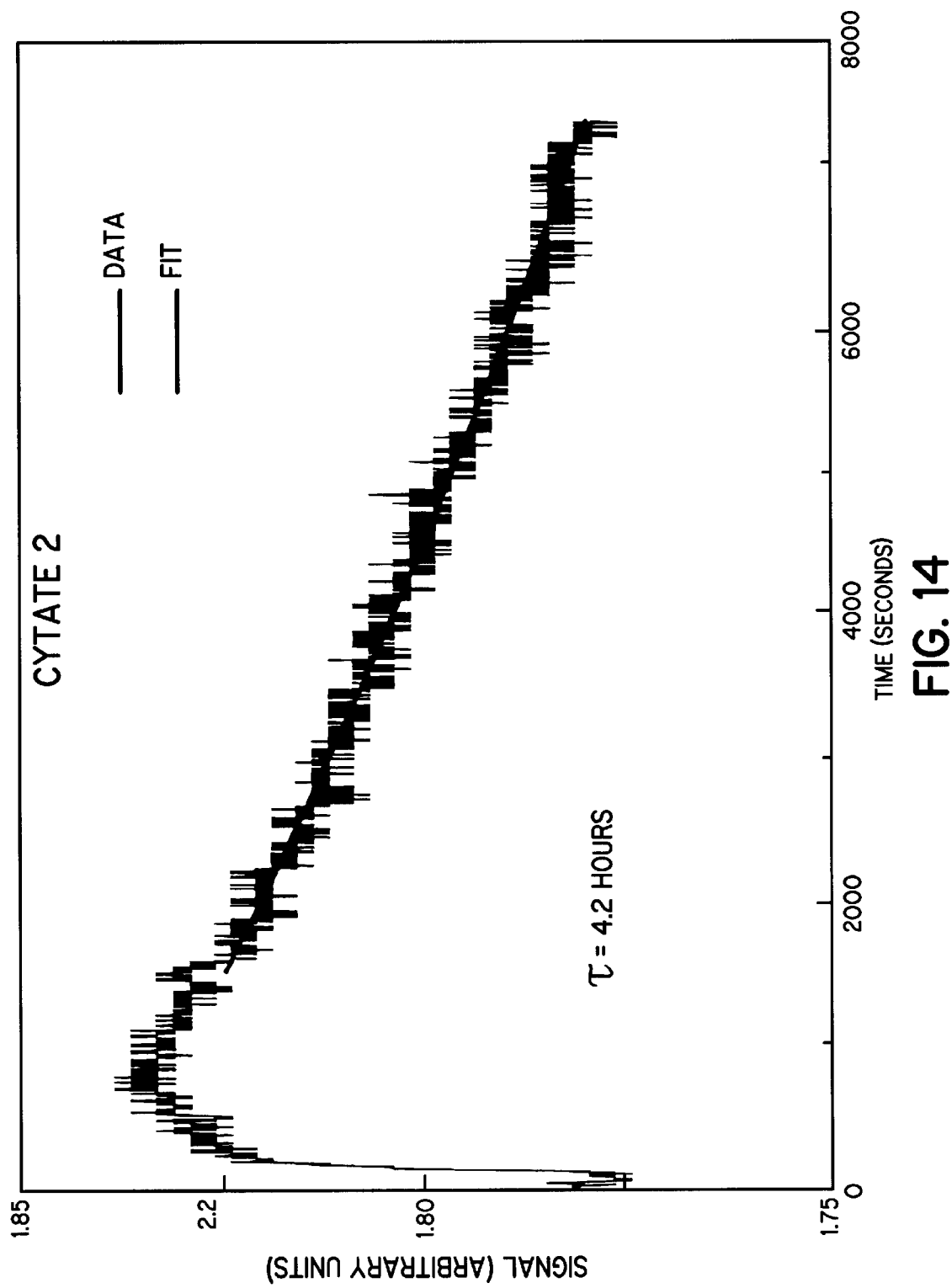
FIG. 14 is the clearance profile of Cytate 2 from the blood of a normal rat.
Figure 15:
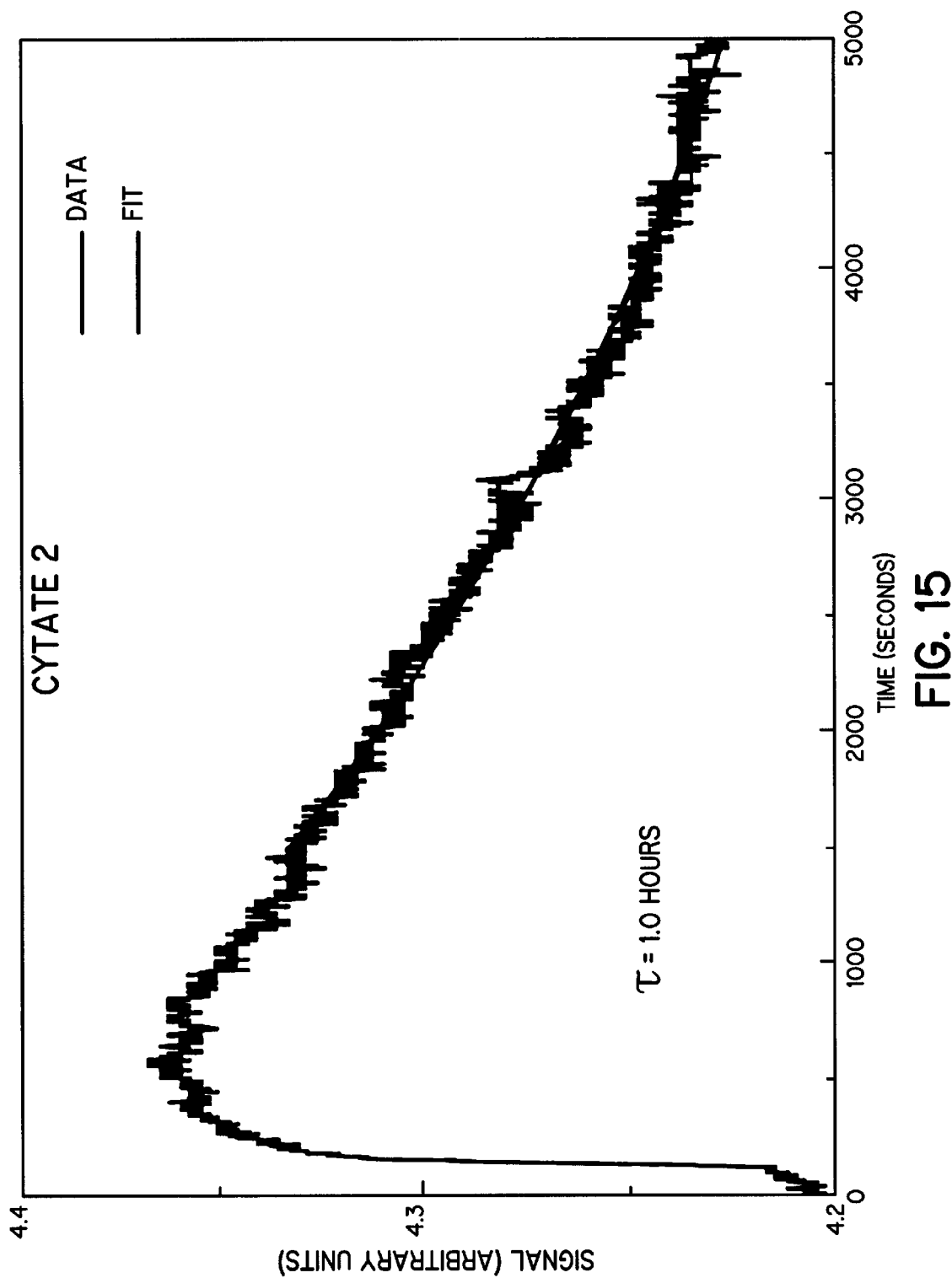
FIG. 15 is the clearance profile of Cytate 2 from the blood of a pancreatic tumor-bearing rat.

FIG. 14 shows the clearance profile of Cytate 2 from the blood of a normal rat, and FIG. 15 shows the clearance profile of Cytate 2 from the blood of a pancreatic tumor (CA20948)-bearing rat, monitored at 830 nm after excitation at 780 nm.

Figure 16:
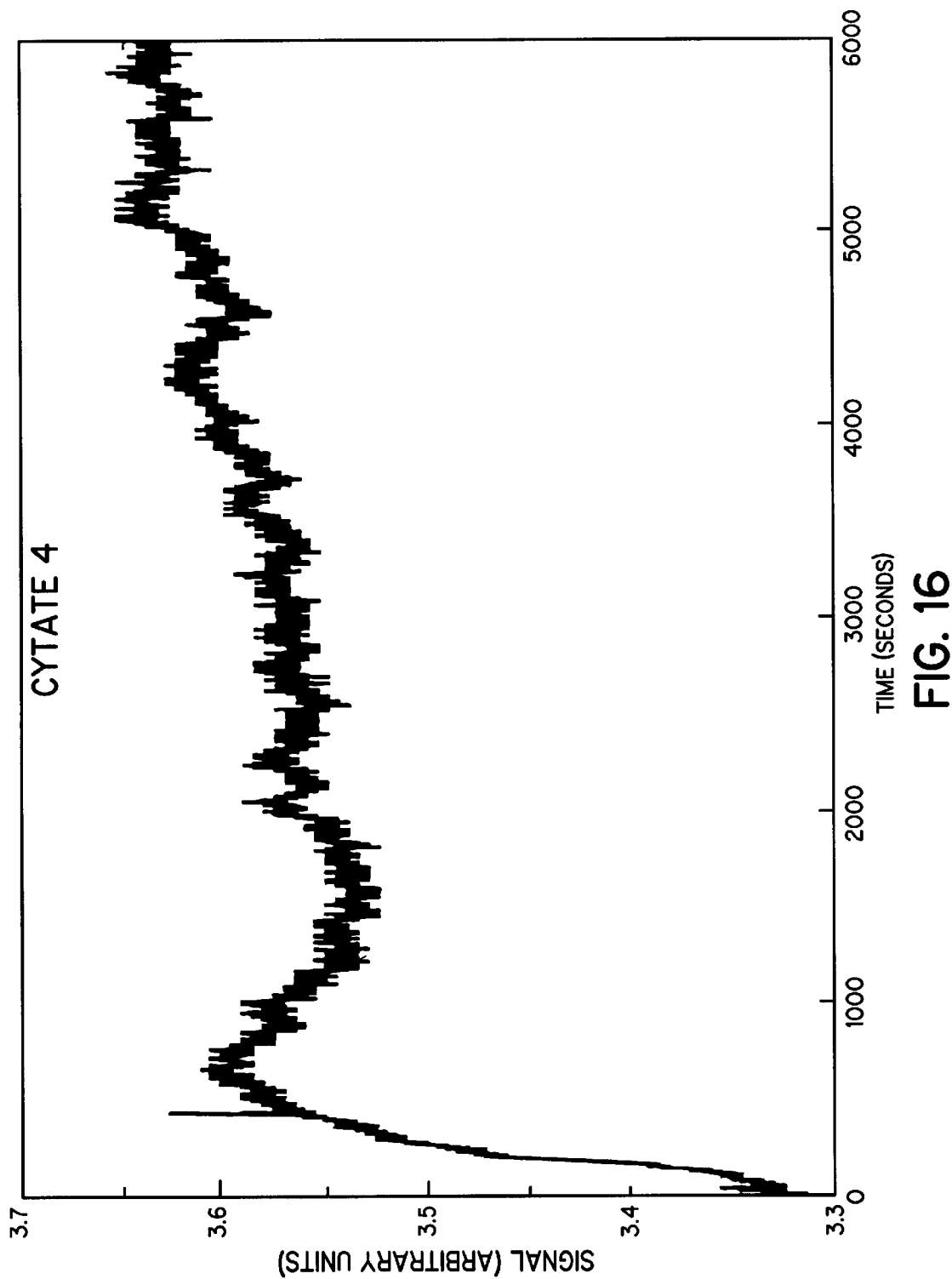
FIG. 16 is the clearance profile of Cytate 4 from the blood of a normal rat.

FIG. 16 shows the clearance profile of Cytate 4 from the blood of a normal rat, monitored at 830 nm after excitation at 780 nm.

It should be understood that the embodiments of the present invention shown and described in the specification are only specific embodiments of inventors who are skilled in the art and are not limiting in any way. Therefore, various changes, modifications, or alterations to those embodiments may be made or resorted to without departing from the spirit of the invention in the scope of the following claims. The references cited are expressly incorporated by reference herein in their entirety.

What is claimed is:

1. A compound of formula

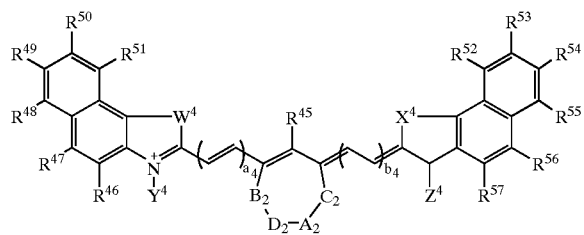

wherein $W^4$ and $X^4$ are —$CR^1R^2$; $Y^4$ is selected from the group consisting of —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—N($R^3$)—$(CH_2)_b$—CONH—Bm, $(CH_2)_a$—N($R^3$)—$(CH_2)_c$—NHCO—Bm, —$(CH_2)_a$—N($R^3$)—$CH_2$—$(CH_2OCH_2)_b$—$CH_2$—CONH—Bm, —$(CH_2)_a$—N($R^3$)—$CH_2$—$(CH_2OCH_2)_b$—$CH_2$—NHCO—Bm, —$CH_2$—$(CH_2OCH_2)_b$—$CH_2$—N($R^3$)—$(CH_2)_a$—CONH—Bm, —$CH_2$—$(CH_2OCH_2)_b$—$CH_2$—N($R^3$)—$(CH_2)_a$—NHCO—Bm, —$CH_2$—$(CH_2OCH_2)_b$—$CH_2$—N($R^3$)—$CH_2$—$(CH_2OCH_2)_d$—CONH—Bm, —$CH_2$—$(CH_2OCH_2)_b$—$CH_2$—N($R^3$)—$CH_2$—$(CH_2OCH_2)_d$—NHCO—Bm, —$(CH_2)_a$—$NR^3R^4$, and —$CH_2(CH_2OCH_2)_b$—$CH_2NR^3R^4$; $Z^4$ is selected from the group consisting of —$(CH_2)_a$—CONH—Dm, —$CH_2$—$(CH_2OCH_2)_b$—$CH_2$CONH—Dm, —$(CH_2)_a$—NHCO—Dm, —$CH_2$—$(CH_2OCH_2)_b$—$CH_2$—NHCO—Dm, —$(CH_2)_a$—N($R^3$)—$(CH_2)_b$—CONH—Dm, $(CH_2)_a$—N($R^3$)—$(CH_2)_c$—NHCO—Dm, —$(CH_2)_a$—N($R^3$)—$CH_2$—$(CH_2OCH_2)_b$—$CH_2$—CONH—Dm, —$(CH_2)_a$—N($R^3$)—$CH_2$—$(CH_2OCH_2)_b$—$CH_2$—NHCO—Dm, —$CH_2$—$(CH_2OCH_2)_b$—$CH_2$—N($R^3$)—$(CH_2)_a$—CONH—Dm, —$CH_2$-$(CH_2OCH_2)_b$—$CH_2$—N($R^3$)—$(CH_2)_a$—NHCO—Dm, —$CH_2$—$(CH_2OCH_2)_b$—$CH_2$—N($R^3$)—$CH_2$—$(CH_2OCH_2)_d$—CONH—Dm, —$CH_2$—$(CH_2OCH_2)_b$—$CH_2$—N($R^3$)—$CH_2$—$(CH_2OCH_2)_d$—NHCO—Dm, —$(CH_2)_a$—$NR^3R^4$, and —$CH_2(CH_2OCH_2)_b$—$CH_2NR^3R^4$; $A_2$ is a single or a double bond; $B_2$, $C_2$, and $D_2$ are independently selected from the group consisting of —O—, —S—, —Se—, —P—, —$CR^1R^2$, —$CR^1$, alkyl, $NR^3$, and —C=O; $A_2$, $B_2$, $O_2$, and $D_2$ may together form a 6- to 12-membered carbocyclic ring or a 6- to 12-membered heterocyclic ring optionally containing one or more oxygen, nitrogen, or sulfur atom; $a_4$ and $b_4$ are independently from 0 to 5; $R^1$ to $R^4$, and $R^{45}$ to $R^{57}$ are independently selected from the group consisting of hydrogen, $C_1$–$C_{10}$ alkyl, $C_5$–$C_{20}$ aryl, $C_1$–$C_{10}$ alkoxyl, $C_1$–$C_{10}$ polyalkoxyalkyl, $C_1$–$C_{20}$ polyhydroxyalkyl, $C_5$–$C_{20}$ polyhydroxyaryl, $C_1$–$C_{10}$ aminoalkyl, cyano, nitro, halogen, saccharide, peptide, —$CH_2(CH_2OCH_2)_b$—$CH_2$—OH, —$(CH_2)_a$—$CO_2H$, —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—OH and —$CH_2$—$(CH_2OCH_2)_b$—$CO_2H$; Bm and Dm are independently selected from the group consisting of a bioactive peptide, a protein, a cell, an antibody, an antibody fragment, a saccharide, a glycopeptide, a peptidomimetic, a drug, a drug mimic, a hormone, a metal chelating agent, a radioactive or nonradioactive metal complex, and an echogenic agent; a and c are independently from 1 to 20; and b and d are independently from 1 to 100.

2. The compound of claim 1 wherein $W_4$ and $X_4$ are independently selected from the group consisting of —$C(CH_3)_2$, —$C((CH_2)_aOH)CH_3$, —$C((CH_2)_aOH)_2$, —$C((CH_2)_aCO_2H)CH_3$, —$C((CH_2)_aCO_2H)_2$, —$C((CH_2)_aNH_2)CH_3$, $C((CH_2)_aNH_2)_2$, and $C((CH_2)_aNR^3R^4)_2$; $Y^4$ is selected from the group consisting of —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—$NR^3R^4$, and —$CH_2(CH_2OCH_3)_b$—$CH_2NR^3R^4$; $Z^4$ is selected from the group consisting of —$(CH_2)_a$—CONH—Dm, —$CH_2$—$(CH_2OCH_2)_b$—$CH_2$—CONH—Dm, —$(CH_2)_a$—NHCO—Dm, —$CH_2$—$(CH_2OCH_2)_b$—$CH_2$—NHCO—Dm, —$(CH_2)_a$—$NR^3R^4$, and —$CH_2(CH_2OCH_2)_b$—$CH_2NR^3R^4$; $A_2$ is a single or a double bond; $B_2$, $C_2$, and $D_2$ are independently selected from the group consisting of —O—, —S—, $NR^3$, $(CH2)_a$—$CR^1R^2$, and —$CR^1$; $A^2$, $B^2$, $C^2$, and $D^2$ may together form a 6- to 10-membered carbocyclic ring or a 6- to 10-membered heterocyclic ring optionally containing one or more oxygen, nitrogen, or sulfur atom; $a_4$ and $b_4$ are independently from 0 to 3; $R^1$ to $R^4$, and $R^{45}$ to $R^{57}$ are independently selected from the group consisting of hydrogen, $C_1$–$C_{10}$ alkyl, $C_5$–$C_{12}$ aryl, $C_1$–$C_{10}$ alkoxyl, $C_1$–$C_{10}$ polyhydroxyalkyl, $C_5$–$C_{12}$ polyhydroxyaryl, $C_1$–$C_{10}$ aminoalkyl, mono- or oligosaccharide, peptide with 2 to 30 amino acid units, —$CH_2(CH_2OCH_2)_b$—$CH_2$—OH, —$(CH_2)_a$—$CO_2H$, —$(CH_2)_a$—CONH—Bm, —$CH_2$—$(CH_2OCH_2)_b$—$CH_2$—CONH—Bm, —$(OH_2)_2$—NHCO—Bm, —$CH_2$—$(CH_2OCH_2)_b$—$CH_2$—NHCO—Bm, —$(CH_2)_aOH$ and —$CH_2$—$(CH_2OCH_2)_b$—$CO_2H$; Bm and Dm are independently selected from the group consisting of a bioactive peptide containing 2 to 30 amino acid units, an antibody, a mono- or oligosaccharide, a glycopeptide, a metal chelating agent, a radioactive or nonradioactive metal complex, and an echogenic agent; a and c are independently from 1 to 10; and b and d are independently from 1 to 30.

3. The compound of claim 2 wherein each $W^4$ and $X^4$ is $C((CH_2)OH)_2$; $Y^4$ is —$(CH_2)_2$—CONH—Bm; $Z^4$ is —$(CH_2)_2$—CONH—Dm; $A_2$ is a single bond; $A_2$, $B_2$, $C_2$, and $D_2$ together form a 6-membered carbocyclic ring; each $a_4$ and $b_4$ is 1; $R^{45}$ is galactose; each $R^{46}$ to $R^{57}$ is hydrogen; Bm is Octreotate; Dm is bombesin (7–14).

4. A method for performing a diagnostic or therapeutic procedure comprising
administering to an individual an effective amount of the compound of formula

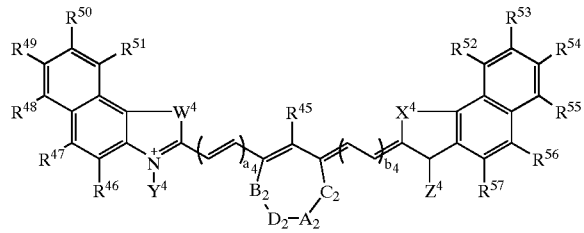

wherein $W^4$ and $X^4$ are —$CR^1R^2$; $Y^4$ is selected from the group consisting of —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$CH_2$—$N(R^3)$—$(CH_2)_b$—CONH—Bm, $(CH_2)_a$—N$(R^3)$—$(CH_2)_c$—NHCO—Bm, —$(CH_2)_a$—N$(R^3)$—$CH_2$—$(CH_2OCH_2)_b$—$CH_2$—NHCO—Bm, $CH_2$—$(CH_2OCH_2)_b$—$CH_2$—N$(R^3)$—$(CH_2)$—CONH—Bm, —$CH_2$—$(CH_2OCH_2)_b$—$CH_2$—N$(R^3)$—$(CH_2)$—NHCO—Bm, —$CH_2$—$(CH_2OCH_2)_b$—$CH_2$—N$(R^3)$—$CH_2$—$(CH_2OCH_3)_d$—CONH—Bm, —$CH_2$—$(CH_2OCH_2)_b$—$CH_2$—N$(R^3)$—$CH_2$—$(CH_2OCH_2)_d$—NHCO—Bm, —$(CH_2)_a$—$NR^3R^4$, and —$CH_2(CH_2OCH_2)_b$—$CH_2NR^3R^4$; $Z^4$ is selected from the group consisting of —$(CH_2)_a$—CONH—Dm, —$CH_2$—$(CH_2OCH_2)_b$—$CH_2$—CONH—Dm, —$(CH_2)_2$—NHCO—Dm, —$CH_2$—$(CH_2OCH_2)_b$—$CH_2$—NHCO—Dm, —$(CH_2)_a$—N$(R^3)$—$(CH_2)_b$—CONH—Dm, $(CH_2)_a$—N$(R^3)$—$(CH_2)_c$—NHCO—Dm, —$(CH_2)_a$—N$(R^3)$—$CH_2$—$(CH_2OCH_2)_b$—$CH_2$—CONH—Dm, —$(CH_2)_a$—N$(R^3)$—$CH_2$—$(CH_2OCH_2)_b$—$CH_2$—NHCO—Dm, —$CH_2$—$(CH_2OCH_2)_b$—$CH_2$—N$(R^3)$—$(CH_2)_a$—CONH—Dm, —$CH_2$—$(CH_2OCH_2)_b$—$CH_2$—N$(R^3)$—$(CH_2)_a$—NHCO—Dm, —$CH_2$—$(CH_2OCH_2)_b$—$CH_2$—N$(R^3)$—$CH_2$—$(CH_2OCH_2)_d$—CONH—Dm, —$CH_2$—$(OH_2OCH_2)_b$—$CH_2$—N$(R^3)$—$CH_2$—$(CH_2OCH_2)_d$—NHCO—Dm, —$(CH_2)_a$—$NR^3R^4$, and —$CH_2(CH_2OCH_2)_b$—$CH_2NR^3R^4$; $A_2$ is a single or a double bond; $B_2$, $C_2$, and $D_2$ are independently selected from the group consisting of —O—, —S—, —Se—, —P—, —$CR^1R^2$, —$CR^1$, alkyl, $NR^3$, and —C=O; $A_2$, $B_2$, $C_2$, and $D_2$ may together form a 6- to 12-membered carbocyclic ring or a 6- to 12-membered heterocyclic ring optionally containing one or more oxygen, nitrogen, or sulfur atom; $a_4$ and $b_4$ are independently from 0 to 5; $R^1$ to $R^4$, and $R^{45}$ to $R^{57}$ are independently selected from the group consisting of hydrogen, $C_1$–$C_{10}$ alkyl, $C_5$–$C_{20}$ aryl, $C_1$–$C_{10}$ alkoxyl, $C_1$–$C_{10}$ polyalkoxyalkyl, $C_1$–$C_{20}$ polyhydroxyalkyl, $C_5$–$C_{20}$ polyhydroxyaryl, $C_1$–$C_{10}$ aminoalkyl, cyano, nitro, halogen, saccharide, peptide, —$CH_2(CH_2OCH_2)_b$—$CH_2$—OH, —$(CH_2)_a$—$CO_2H$, —$(CH_2)_2CONH$—Bm, —$CH_2$—$(OH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—OH and —$CH_2$—$(CH_2OCH_2)_b$—$CO_2H$; Bm and Dm are independently selected from the group consisting of a bioactive peptide, a protein, a cell, an antibody, an antibody fragment, a saccharide, a glycopeptide, a peptidomimetic, a drug, a drug mimic, a hormone, a metal chelating agent, a radioactive or nonradioactive metal complex, and an echogenic agent; a and c are independently from 1 to 20; and b and d are independently from 1 to 100, activating the compound using light, and performing the diagnostic or therapeutic procedure.

5. The method of claim 4 comprising administering to an individual an effective amount of the compound wherein $W^4$ and $X^4$ are independently selected from the group consisting of —$C(CH_3)_2$, —$C((CH_2)_aOH)CH_3$, —$C((CH_2)_aOH)_2$, —$C((CH_2)_aCO_2H)CH_3$, —$C((CH_2)_aCO_2H)_2$, —$C((CH_2)_aNH_2)CH_3$, $C((CH_2)_aNH_2)_2$, and $C((CH_2)_aNR^3R^4)_2$; $Y^4$ is selected from the group consisting of —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—$NR^3R^4$, and —$CH_2(CH_2OCH_2)_b$—$CH_2NR^3R^4$; $Z^4$ is selected from the group consisting of —$(CH_2)_a$—CONH—Dm, —$CH_2$—$(CH_2OCH_2)_b$—$CH_2$—CONH—Dm, —$(CH_2)_a$NHCO—Dm, —$CH_2$—$(CH_2OCH_2)_b$—$CH_2$—NHCO—Dm, —$(CH_2)_a$—$NR^3R^4$, and —$CH_2(CH_2OCH_2)_b$—$CH_2NR^3R^4$; $A_2$ is a single or a double bond; $B_2$, $C_2$, and $D_2$ are independently selected from the group consisting of —O—, —S—, $NR^3$, ($CH2)_2$—$CR^1R^2$, and —$CR^1$; $A_2$, $B_2$, $C_2$, and $D_2$ may together form a 6- to 10-membered carbocyclic ring or a 6- to 10-membered heterocyclic ring optionally containing one or more oxygen, nitrogen, or sulfur atom; $a_4$ and $b_4$ are independently from 0 to 3; $R^1$ to $R^4$, and $R^{45}$ to $R^{57}$ are independently selected from the group consisting of hydrogen, $C_1$–$C_{10}$ alkyl, $C_5$–$C_{12}$ aryl, $C_1$–$C_{10}$ alkoxyl, $C_1$–$C_{10}$ polyhydroxyalkyl, $C_5$–$C_{12}$ polyhydroxyaryl, $C_1$–$C_{10}$ aminoalkyl, mono- or oligosaccharide, peptide with 2 to 30 amino acid units, —$CH_2(CH_2OCH_2)_b$—$CH_2$—OH, —$(CH_2)_a$—$CO_2H$, —$(CH_2)_a$—CONH—Bm, —$CH_2$—$(CH_2OCH_2)_b$—$CH_2$—CONH—Bm, —$(CH_2)_a$NHCO—Bm, —$CH_2$—$(CH_2OCH_2)_b$—$CH_2$—NHCO—Bm, —$(CH_2)_a$—OH and —$CH_2$—$(CH_2OCH_2)_b$—$CO_2H$; Bm and Dm are independently selected from the group consisting of a bioactive peptide containing 2 to 30 amino acid units, an antibody, a mono- or oligosaccharide, a glycopeptide, a metal chelating agent, a radioactive or nonradioactive metal complex, and an echogenic agent; a and c are independently from 1 to 10; and b and d are independently from 1 to 30.

6. The method of claim 5 comprising administering to an individual an effective amount of the compound wherein each of $W^4$ and $X^4$ is $C((CH_2)OH)_2$; $Y^4$ is —$(CH_2)_2$—CONH—Bm; $Z^4$ is —$(CH_2)_2$—CONH—Dm; $A_2$ is a single bond; $A_2$, $B_2$, $C_2$, and $D_2$ together form a 6-membered carbocyclic ring; each $a_4$ and $b_4$ is 1; $R^{45}$ is galactose; each $R^{46}$ to $R^{57}$ is hydrogen; Bm is Octreotate; Dm is bombesin (7–14).

7. The method of claim 4 wherein said procedure utilizes light of wavelength in the region of 350–1300 nm.

8. The method of claim 4 wherein the diagnostic procedure is optical tomography.

9. The method of claim 4 wherein said diagnostic procedure is fluorescence endoscopy.

10. The method of claim 4 further comprising monitoring a blood clearance profile of said compound by a method selected from the group consisting of fluorescence, absorbance, and light scattering, wherein light of wavelength in the region of 350–1300 nm is used.

11. The method of claim 4 wherein said procedure further comprises imaging and therapy, wherein said imaging and therapy is selected from the group consisting of absorption, light scattering, photoacoustic and sonofluoresence technique.

12. The method of claim 4 wherein said procedure is capable of diagnosing atherosclerotic plaques and blood clots.

13. The method of claim 4 wherein said procedure comprises administering localized therapy.

14. The method of claim 4 wherein said therapeutic procedure comprises photodynamic therapy.

15. The method of claim 4 wherein said therapeutic procedure comprises laser assisted guided surgery for the detection of micrometastases.

16. The method of claim 4 further comprising adding a biocompatible organic solvent at a concentration of one to fifty percent to the compound to prevent in vivo or in vitro fluorescence quenching.

17. The method of claim 16 wherein said compound is dissolved in a medium comprising one to fifty percent dimethyl sulfoxide.

18. A composition comprising a cyanine dye bioconjugate of formula

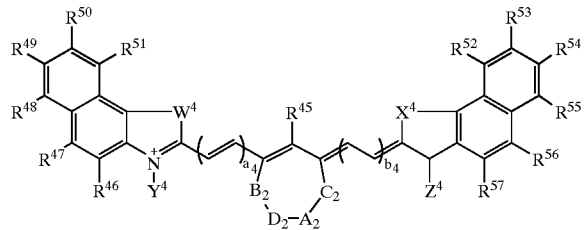

wherein $W^4$ and $X^4$ are —$CR^1R^2$; $Y^4$ is selected from the group consisting of —$(CH_2)_a$—CONH—Bm, —$CH_2$—$(CH_2OCH_2)_b$—$CH_2$—CONH—Bm, —$(CH_2)_a$—NHCO—Bm, —$OH_2$—$(CH_2OCH_2)_b$—$CH_2$—NHCO—Bm, —$(CH_2)_a$—$N(R^3)$—$(CH_2)_b$—CONH—Bm, $(CH_2)_a$—N$(R^3)$—$(CH_2)_c$—NHCO—Bm, —$(CH_2)_a$—$N(R^3)$$CH_2$—$(CH_2OCH_2)_b$—$CH_2$—CONH—Bm, —$(CH_2)_a$—$N(R^3)$—$CH^2$—$(CH_2OCH_2)_b$—$CH_2$—NHCO—Bm, —$CH_2$—$(CH_2OCH_2)_b$—$CH_2$—$N(R^3)$—$(CH_2)_a$—CONH—Bm, —$CH_2$—$(CH_2OCH_2)_b$—$CH_2$—$N(R^3)$—$(CH_2)_a$NHCO—Bm, —$CH_2$—$(CH_2OCH_2)_b$—$CH_2$—$N(R^3)$—$CH_2$—$(CH_2OCH_2)_d$—CONH—Bm, —$CH_2$—$(CH_2OCH_2)_b$—$CH_2$—$N(R^3)$—$CH_2$—$(CH_2OCH_2)_d$—NHCO—Bm, —$(CH_2)_a$—$NR^3R^4$, and —$CH_2(CH_2OCH_2)_b$—$CH_2NR^3R^4$; $Z^4$ is selected from the group consisting of —$(CH_2)_a$—CONH—Dm, —$CH_2$—$(CH_2OCH_2)_b$—$CH_2$—CONH—Dm, —$(CH_2)_a$—NHCO—Dm, —$CH_2$—$(CH_2OCH_2)_b$—$CH_2$—NHCO—Dm, —$(CH_2)_a$—$N(R^3)$—$(CH_2)_c$—NHCO—Dm, —$(CH_2)_a$—$N(R^3)$—$CH_2$—$(CH_2OCH_2)_b$—$CH_2$—CONH—Dm, —$(CH_2)_a$—$N(R^3)$—$CH_2$—$(CH_2OCH_2)_b$—$CH_2$—NHCO—Dm, —$CH_2$—$(CH_2OCH_2)_b$—$CH_2$—$N(R^3)$—$(CH_2)_a$—CONH—Dm, —$CH_2$—$(CH_2OCH_2)_b$—$CH_2$—$N(R^3)_a$—$(CH_2)_a$—NHCO—Dm, —$CH_2$—$(CH_2OCH_2)_b$—$CH_2$—$N(R^3)$—$CH_2$—$(CH_2OCH_2)_d$—CONH—Dm, —$CH_2$—$(CH_2OCH_2)_b$—$CH_2$—$N(R^3)$—$CH_2$—$(CH_2OCH_2)_d$—NHCO—Dm, —$(CH_2)_a$—$NR^3R^4$, and —$CH_2(CH_2OCH_2)_b$—$CH_2NR^3R^4$; $A_2$ is a single or a double bond; $B_2$, $C_2$, and $D_2$ are independently selected from the group consisting of —O—, —S—, —Se—, —P—, —$CR^1R^2$, —$CR^1$, alkyl, $NR^3$, and —C=O; $A_2$, $B_2$, $C_2$, and $D_2$ may together form a 6- to 12-membered carbocyclic ring or a 6- to 12-membered heterocyclic ring optionally containing one or more oxygen, nitrogen, or sulfur atom; $a_4$ and $b_4$ are independently from 0 to 5; $R^1$ to $R^4$, and $R^{45}$ to $R^{57}$ are independently selected from the group consisting of hydrogen, $C_1$–$C_{10}$ alkyl, $C_5$–$C_{20}$ aryl, $C_1$–$C_{10}$ alkoxyl, $C_1$–$C_{20}$ polyalkoxyalkyl, $C_1$–$C_{20}$ polyhydroxyalkyl, $C_5$–$C_{20}$ polyhydroxyaryl, $C_1$–$C_{10}$ aminoalkyl, cyano, nitro, halogen, saccharide, peptide, —$CH_2(CH_2OCH_2)_b$—$CH_2$—OH, —$(CH_2)_a$—$CO_2H$, —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—OH and —$CH_2$—$(CH_2OCH_2)_b$—$CO_2H$; Bm and Dm are independently selected from the group consisting of a bioactive peptide, a protein, a cell, an antibody, an antibody fragment, a saccharide, a glycopeptide, a peptidomimetic, a drug, a drug mimic, a hormone, a metal chelating agent, a radioactive or nonradioactive metal complex, and an echogenic agent; a and c are independently from 1 to 20; and b and d are independently vary from 1 to 100, and a pharmaceutically acceptable carrier or excipient.

19. The composition of claim 18 wherein $W^4$ and $X^4$ are independently selected from the group consisting of —$C(CH_3)_2$, —$C((CH_2)_aOH)CH_3$, $C((CH_2)_aOH)_2$, —$C((CH_2)_aCO_2H)CH_3$, —$C((CH_2)_aCO_2H)_2$, —$C((CH_2)_aNH_2)CH_3$, $C((CH_2)_aNH_2)_2$, and $C((CH_2)_aNR^3R^4)_2$; $Y^4$ is selected from the group consisting of —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—$NR^3R^4$, and —$CH_2(CH_2OCH_2)_b$—$CH_2NR^3R^4$; $Z^4$ is selected from the group consisting of —$(CH_2)_a$—CONH—Dm, —$CH_2$—$(CH_2OCH_2)_b$—$CH_2$—CONH—Dm, —$(CH_2)_a$—NHCO—Dm, —$OH_2$—$(CH_2OCH_2)_b$—$CH_2$—NHCO—Dm, —$(CH_2)_a$—$NR^3R^4$, and —$CH_2(CH_2OCH_2)_b$—$CH_2NR^3R^4$; $A_2$ is a single or a double bond; $B_2$, $C_2$, and $D_2$ are independently selected from the group consisting of —O—, —S—, $NR^3$, $(CH_2)_a$—$CR^1R^2$, and —$CR^1$; $A_2$, $B_2$, $C_2$, and $D_2$ may together form a 6- to 10-membered carbocyclic ring or a 6- to 10-membered heterocyclic ring optionally containing one or more oxygen, nitrogen, or sulfur atom; $a_4$ and $b_4$ are independently from 0 to 3; $R^1$ to $R^4$, and $R^{45}$ to $R^{57}$ are independently selected from the group consisting of hydrogen, $C_1$–$C_{10}$ alkyl, $C_5$–$C_{12}$ aryl, $C_1$–$C_{10}$ alkoxyl, $C_1$–$C_{10}$ polyhydroxyalkyl, $C_5$–$C_{12}$ polyhydroxyaryl, $C_1$–$C_{10}$ aminoalkyl, mono- or oligosaccharide, peptide with 2 to 30 amino acid units, —$CH_2(CH_2OCH_2)_b$—$CH_2$—OH, —$(CH_2)_a$—$CO_2H$, —$(CH_2)_a$—CONH—Bm, —$CH_2$—$(CH_2OCH_2)_b$—$CH_2$—CONH—Bm, —$(CH_2)_a$—NHCO—Bm, —$CH_2$—$(CH_2OCH_2)_b$—$CH_2$—NHCO—Bm, —$(CH_2)_a$—OH and —$CH_2$—$(CH_2OCH_2)_b$—$CO_2H$; Bm and Dm are independently selected from the group consisting of a bioactive peptide containing 2 to 30 amino acid units, an antibody, a mono- or oligosaccharide, a glycopeptide, a metal chelating agent, a radioactive or nonradioactive metal complex, and an echogenic agent; a and c are independently from 1 to 10; and b and d are independently from 1 to 30.

20. The composition of claim 19 wherein each of $W^4$ and $X^4$ is $C((CH_2)OH)_2$; $Y^4$ is —$(CH_2)_2$—CONH—Bm; $Z^4$ is —$(CH_2)_2$—CONH—Dm; $A_2$ is a single bond; $A_2$, $B_2$, $C_2$, and $D_2$ together form a 6-membered carbocyclic ring; $a_4$ and $b_4$ are independently galactose; each of $R^{46}$ to $R^{57}$ is hydrogen; Bm is Octreotate; and Dm is bombesin (7–14).

* * * * *

UNITED STATES PATENT AND TRADEMARK OFFICE
CERTIFICATE OF CORRECTION

PATENT NO. : 6,641,798 B2
DATED : November 4, 2003
INVENTOR(S) : Achilefu et al.

It is certified that error appears in the above-identified patent and that said Letters Patent is hereby corrected as shown below:

Column 1,
Line 40, "Sulformdocyanine" should be -- Sulfoindocyanine --

Column 2,
Line 47, "271:58-65." should be -- 271:58-65.) --
Line 66, "near infrared region (beyond 800 mm), and ..." should be -- near infrared region (beyond 800 mm), and... --

Column 3,
Line 44, "$-CH_2(CH_2OCH_2)_b-CH_2NR^3R$ different and are selected..." should be -- $-CH_2(CH_2OCH_2)_b-CH_2NR^3R^4$; $A_1$ is a single or a double bond; $B_1$, $C_1$, and $D_1$ may be the same or different and are selected ... --

Column 4,
Line 19, "$-(CH_2)-NHCO-$" should be -- $-(CH_2)_a-NHCO-$ --
Line 21, "$(CH_2)_a$" should be -- $-(CH_2)_a-$ --
Line 31, "$Z^4$ is selected from the group consisting of $-(CH_2)-$" should be -- $Z^4$ is selected from the group consisting of $-(CH_2)_a-$ --
Line 45, "$A_2$ is a single or a double b or different and ..." should be -- $A_2$ is a single or a double bond; $B_2$, $C_2$, and $D_2$ may the same or different and ... --

Column 5,
Line 20, "$-(CH_2)_b-CH_2-CONH-Bm, -(CH_2),$" should be -- $-CH_2-(CH_2OCH_2)_b-CH_2-CONH-Bm, -(CH_2)_a-$ --
Line 35, "$B_3$, $C_3$ or different..." should be -- $B_3$, $C_3$, and $D_3$, may be the same or different... --

Column 6,
Line 24, "$-(CH_2CH_2)_b-$" should be -- $-CH_2$ --
Line 27, "$-CH_2(CH_2CH_2)_b-$" should be -- $-CH_2(CH_2OCH_2)_b-$ --
Line 31, "$-(CH_2)-N(R_3)-$" should be -- $-(CH_2)_a-N(R_3)-$ --

Column 8,
Line 21, "R =COOH, ... SO3;" should be -- $R'$ =COOH, ...$SO_3^-$; --
Line 36, "$-C((CH_2)OH)CH_3-$" should be -- $-C((CH_2)_aOH)CH_3-$ --

Column 12,
Line 39, "Synthesis of Bisethylcarboxymethvlindocyanine dye" should be -- Synthesis of Bisethylcarboxymethylindocyanine dye --

UNITED STATES PATENT AND TRADEMARK OFFICE
CERTIFICATE OF CORRECTION

PATENT NO. : 6,641,798 B2
DATED : November 4, 2003
INVENTOR(S) : Achilefu et al.

It is certified that error appears in the above-identified patent and that said Letters Patent is hereby corrected as shown below:

Column 16,
Line 58, "place into the later tail vein of the rat." should be -- placed into the lateral tail vein of the rat --

Column 17,
Line 17, "imaged at two minutes (FIG. 7C) and minutes (FIG. 7D)" should be -- "imaged at two minutes (FIG. 7C) and 30 minutes (FIG. 7D) --
Line 50, "acinar carcinoma were induced by" should be -- acinar carcinoma was induced by --

Column 18,
Line 16, "cyano-Octreotates (Cytate 1 and Cytate 2) was prepared" should be -- cyano-Octreotates (Cyate 1 and Cytate 2) were prepared --

Column 19,
Line about 38 and 58, "MOD RES" should be -- MOD_RES --

Column 21,
Line about 5, 55, and 60, "MOD RES" should be MOD_RES --

Column 23,
Line 5, "MOD RES" should be -- MOD_RES --
Line 59, "$O_2$" should be -- $C_2$ --

Column 24,
Line 37, "...$(CH_2OCH_3)_b$–" should be -- ...$(CH_2OCH_2)_b$– --
Line 44, " $(CH2)_a$" should be -- $(CH_2)_a$ --
Line 44, "$A^2$, $B^2$, $C^2$, and $D^2$" should be -- $A_2$, $B_2$, $C_2$, $D_2$ --
Line 55, "–$(OH_2)_2$–" should be -- –$(CH_2)_a$– --
Line 57, "...–$(CH_2)_a$OH and ..." should be -- ...–$(CH_2)_a$–OH and... --

Column 25,
Line 24, "$(CH_2OCH_2)_b$–$CH_2$–NHCO–Bm," should be -- $(CH_2OCH_2)_b$–$CH_2$–CONH–Bm, –$(CH_2)_a$-N®-$CH_2$-$(CH_2$-$OCH_2)_b$-$CH_2$NHCO-Bm, --
Line 24, "$CH_2$–" should be -- –$CH_2$– --
Lines 25 and 26, "–$(CH_2)$--" should be -- –$(CH_2)_a$ --
Line 33, "–$(CH_2)_2$–" should be -- –$(CH_2)_a$– --
Line 42, "–$(OH_2OCH_2)_b$–" should be -- –$(CH_2OCH_2)_b$– --
Line 57, "–$(CH_2)_2$–CONH–Bm,..." should be -- –$(CH_2)_a$–CONH–Bm,... --
Line 58, "...–$(OH_2OCH_2)_b$– ..." should be -- ....–$(CH_2OCH_2)_b$– ... --

UNITED STATES PATENT AND TRADEMARK OFFICE
CERTIFICATE OF CORRECTION

PATENT NO. : 6,641,798 B2
DATED : November 4, 2003
INVENTOR(S) : Achilefu et al.

It is certified that error appears in the above-identified patent and that said Letters Patent is hereby corrected as shown below:

Column 26,
Line 14, "$-(CH_2)_a-NHCO-$" should be -- $-(CH_2)_a-NHCO-$ --
Line 19, "$(CH2)_2-...$" should be -- $(CH_2)_a-...$ --
Line 30, "$-(CH_2)_aNHCO--$" should be -- $-(CH_2)_a-NHCO--$ --

Column 27,
Line 29, "$-OH_2--$" should be -- $-CH_2-$ --
Line 33, "$-CH^2-$" should be -- $-CH_2-$ --
Line 35, "$-(CH_2)_aNHCO-$" should be -- $-(CH_2)_a-NHCO$ --
Line 43, "$-(CH_2)_c...$" should be -- $-(CH_2)_b...$ --
Line 44, before "NHCO–Dm ..." insert -- ....$-CONH-Dm, (CH_2)_a-N(R_3)-(CH_2)_c$ ... --
Line 48, "$-N(R^3)_a-$" should be -- $-N(R^3)-$ --

Column 28,
Line 29, "$-OH_2-$" should be -- $-(CH_2)-$ --

Signed and Sealed this

Fourteenth Day of September, 2004

JON W. DUDAS
*Director of the United States Patent and Trademark Office*

UNITED STATES PATENT AND TRADEMARK OFFICE
CERTIFICATE OF CORRECTION

PATENT NO. : 6,641,798 B2
DATED : November 4, 2003
INVENTOR(S) : Achilefu et al.

It is certified that error appears in the above-identified patent and that said Letters Patent is hereby corrected as shown below:

Column 1,
Line 40, "Sulformdocyanine" should be -- Sulfoindocyanine --

Column 2,
Line 47, "271:58-65." should be -- 271:58-65.) --
Line 66, "near infrared region (beyond 800 mm), and ..." should be -- near infrared region (beyond 800 nm), and... --

Column 3,
Line 44, "$-CH_2(CH_2OCH_2)_b-CH_2NR^3R$ different and are selected..." should be -- $-CH_2(CH_2OCH_2)_b-CH_2NR^3R^4$; $A_1$ is a single or a double bond; $B_1$, $C_1$, and $D_1$ may be the same or different and are selected ... --

Column 4,
Line 19, "$-(CH_2)-NHCO-$" should be -- $-(CH_2)_a-NHCO-$ --
Line 21, "$(CH_2)_a$" should be -- $-(CH_2)_a-$ --
Line 31, "$Z^4$ is selected from the group consisting of $-(CH_2)-$" should be -- $Z^4$ is selected from the group consisting of $-(CH_2)_a-$ --
Line 45, "$A_2$ is a single or a double b or different and ..." should be -- $A_2$ is a single or a double bond; $B_2$, $C_2$, and $D_2$ may the same or different and ... --

Column 5,
Line 20, "$-(CH_2)_b-CH_2-CONH-Bm, -(CH_2),$" should be -- $-CH_2-(CH_2OCH_2)_b-CH_2-CONH-Bm, -(CH_2)_a-$ --
Line 35, "$-(CH_2),$" should read -- $-(CH_2)_a-$ --
Line 44, "$B_3$, $C_3$ or different..." should be -- $B_3$, $C_3$, and $D_3$, may be the same or different... --

Column 6,
Line 24, "$-(CH_2CH_2)_b-$" should be -- $-(CH_2OCH_2)_b-$ --
Line 25, "$CH_2-$" should be -- $-CH_2-$ --
Line 27, "$-CH_2(CH_2CH_2)_b-$" should be -- $-CH_2(CH_2OCH_2)_b-$ --
Line 31, "$-(CH_2)-N(R_3)-$" should be -- $-(CH_2)_a-N(R_3)-$ --

Column 8,
Line 21, "R =COOH, ... SO3;" should be -- R' =COOH, ...$SO_3^-$; --
Line 36, "$-C((CH_2)OH)CH_3-$" should be -- $-C((CH_2)_aOH)CH_3-$ --

Column 12,
Line 39, "Synthesis of Bisethylcarboxymethvlindocyanine dye" should be -- Synthesis of Bisethylcarboxymethylindocyanine dye --

UNITED STATES PATENT AND TRADEMARK OFFICE
CERTIFICATE OF CORRECTION

PATENT NO. : 6,641,798 B2
DATED : November 4, 2003
INVENTOR(S) : Achilefu et al.

It is certified that error appears in the above-identified patent and that said Letters Patent is hereby corrected as shown below:

Column 16,
Line 58, "place into the later tail vein of the rat." should be -- placed into the lateral tail vein of the rat --

Column 17,
Line 17, "imaged at two minutes (FIG. 7C) and minutes (FIG. 7D)" should be -- "imaged at two minutes (FIG. 7C) and 30 minutes (FIG. 7D) --
Line 50, "acinar carcinoma were induced by" should be -- acinar carcinoma was induced by --

Column 18,
Line 16, "cyano-Octreotates (Cytate 1 and Cytate 2) was prepared" should be -- cyano-Octreotates (Cyate 1 and Cytate 2) were prepared --

Column 19,
Line about 38 and 58, "MOD RES" should be -- MOD_RES --

Column 21,
Line about 5, 55, and 60, "MOD RES" should be -- MOD_RES --

Column 23,
Line 5, "MOD RES" should be -- MOD_RES --
Line 59, "$O_2$" should be -- $C_2$ --

Column 24,
Line 37, "...$(CH_2OCH_3)_b$–" should be -- ...$(CH_2OCH_2)_b$– --
Line 44, "$(CH2)_a$" should be -- $(CH_2)_a$ --
Line 44, "$A^2$, $B^2$, $C^2$, and $D^2$" should be -- $A_2$, $B_2$, $C_2$, $D_2$ --
Line 55, "–$(OH_2)_2$–" should be -- –$(CH_2)_a$– --
Line 57, "...–$(CH_2)_a OH$ and ..." should be -- ...–$(CH_2)_a$–OH and... --

Column 25,
Line 24, "$(CH_2OCH_2)_b$–$CH_2$–NHCO–Bm," should be -- $(CH_2OCH_2)_b$–$CH_2$–CONH–Bm, –$(CH_2)_a$-$NR^3$-$CH_2$-$(CH_2$-$OCH_2)_b$-$CH_2$NHCO-Bm, --
Line 24, "$CH_2$–" should be -- –$CH_2$– --
Lines 25 and 26, "–$(CH_2)$--" should be -- –$(CH_2)_a$ --
Line 33, "–$(CH_2)_2$–" should be -- –$(CH_2)_a$– --
Line 42, "–$(OH_2OCH_2)_b$–" should be -- –$(CH_2OCH_2)_b$– --
Line 57, "–$(CH_2)_2$–CONH–Bm,..." should be -- –$(CH_2)_a$–CONH–Bm,... --
Line 58, "...–$(OH_2OCH_2)_b$– ..." should be -- ....–$(CH_2OCH_2)_b$– ... --

UNITED STATES PATENT AND TRADEMARK OFFICE
CERTIFICATE OF CORRECTION

PATENT NO.     : 6,641,798 B2
DATED          : November 4, 2003
INVENTOR(S)    : Achilefu et al.

It is certified that error appears in the above-identified patent and that said Letters Patent is hereby corrected as shown below:

Column 26,
Line 14, "–$(CH_2)_a$–NHCO–" should be -- –$(CH_2)_a$–NHCO– --
Line 19, "$(CH2)_2$–..." should be -- $(CH_2)_a$–... --
Line 30, "–$(CH_2)_a$NHCO--" should be -- –$(CH_2)_a$–NHCO-- --

Column 27,
Line 29, "–$OH_2$--" should be -- –$CH_2$– --
Line 33, "–$CH^2$–" should be -- –$CH_2$– --
Line 35, "–$(CH_2)_a$NHCO–" should be -- –$(CH_2)_a$–NHCO --
Line 43, "–$(CH_2)_c$..." should be -- –$(CH_2)_b$... --
Line 44, before "NHCO–Dm ..." insert -- ....–CONH-Dm, $(CH_2)_a$-$N(R_3)$-$(CH_2)_c$ ... --
Line 48, "–$N(R^3)_a$–" should be -- –$N(R^3)$– --

Column 28,
Line 29, "–$OH_2$–" should be -- –$(CH_2)$– --

This certificate supersedes Certificate of Correction issued September 14, 2004.

Signed and Sealed this

Twenty-first Day of December, 2004

JON W. DUDAS
*Director of the United States Patent and Trademark Office*

SEQUENCE LISTING

<160> NUMBER OF SEQ ID NOS: 8

<210> SEQ ID NO 1
<211> LENGTH: 8
<212> TYPE: PRT
<213> ORGANISM: Artificial Sequence
<220> FEATURE:
<221> NAME/KEY: MOD RES
<222> LOCATION: (1)...(7)
<223> OTHER INFORMATION: Xaa at location 1 represents D-Phe. Artificial
      sequence is completely synthesized.
<223> OTHER INFORMATION: Xaa at locations 2 and 7 represents Cys with
      an intramolecular disulfide bond between two Cys
      amino acids. Artificial sequence is completely synthesized.
<223> OTHER INFORMATION: Xaa at location 4 represents D-Trp. Artificial
      sequence is completely synthesized.

<400> SEQUENCE: 1

Xaa Xaa Tyr Xaa Lys Thr Xaa Thr
1               5

<210> SEQ ID NO 2
<211> LENGTH: 8
<212> TYPE: PRT
<213> ORGANISM: Artificial Sequence
<220> FEATURE:
<221> NAME/KEY: MOD RES
<222> LOCATION: (1)...(8)
<223> OTHER INFORMATION: Xaa at location 1 represents D-Phe. Artificial
      sequence is completely synthesized.
<223> OTHER INFORMATION: Xaa at locations 2 and 7 represents Cys with an
      intramolecular disulfide bond between two Cys amino acids.
      Artificial sequence is completely synthesized.
<223> OTHER INFORMATION: Xaa at location 4 represents D-Trp. Artificial
      sequence is completely synthesized.
<223> OTHER INFORMATION: Xaa at location 8 represents Thr-OH. Artificial
      sequence is completely synthesized.

<400> SEQUENCE: 2

Xaa Xaa Tyr Xaa Lys Thr Xaa Xaa
1               5

```
<210> SEQ ID NO 3
<211> LENGTH: 11
<212> TYPE: PRT
<213> ORGANISM: Peptide
<220> FEATURE:
<221> NAME/KEY: MOD RES
<222> LOCATION: (1)...(0)

<400> SEQUENCE: 3

Gly Ser Gly Gln Trp Ala Val Gly His Leu Met
 1               5                  10

<210> SEQ ID NO 4
<211> LENGTH: 11
<212> TYPE: PRT
<213> ORGANISM: Peptide
<220> FEATURE:
<221> NAME/KEY: MOD_RES
<222> LOCATION: (1)...(0)

<400> SEQUENCE: 4

Gly Asp Gly Gln Trp Ala Val Gly His Leu Met
 1               5                  10

<210> SEQ ID NO 5
<211> LENGTH: 8
<212> TYPE: PRT
<213> ORGANISM: Peptide
<220> FEATURE:
<221> NAME/KEY: MOD_RES
<222> LOCATION: (1)...(0)

<400> SEQUENCE: 5

Asp Tyr Met Gly Trp Met Asp Phe
 1               5

<210> SEQ ID NO 6
<211> LENGTH: 8
<212> TYPE: PRT
<213> ORGANISM: Artificial Sequence
<220> FEATURE:
<221> NAME/KEY: MOD RES
<222> LOCATION: (1)...(6)
<223> OTHER INFORMATION: Xaa at locations 3 and 6 represents Norleucine.
      Artificial sequence is completely synthesized.

<400> SEQUENCE: 6

Asp Tyr Xaa Gly Trp Xaa Asp Phe
 1               5

<210> SEQ ID NO 7
<211> LENGTH: 8
<212> TYPE: PRT
<213> ORGANISM: Artificial Sequence
<220> FEATURE:
<221> NAME/KEY: MOD RES
<222> LOCATION: (1)...(6)
<223> OTHER INFORMATION: Xaa at location 1 represents D-Asp. Artificial
      sequence is completely synthesized.
<223> OTHER INFORMATION: Xaa at locations 3 and 6 represents Norleucine.
      Artificial sequence is completely synthesized.

<400> SEQUENCE: 7

Xaa Tyr Xaa Gly Trp Xaa Asp Phe
 1               5

<210> SEQ ID NO 8
```

```
<211> LENGTH: 8
<212> TYPE: PRT
<213> ORGANISM: Artificial Sequence
<220> FEATURE:
<221> NAME/KEY: MOD RES
<222> LOCATION: (1)...(1)
<223> OTHER INFORMATION: Xaa at location 1 represents D-Lys. Artificial
      sequence is completely synthesized.

<400> SEQUENCE: 8

Xaa Pro Arg Arg Pro Tyr Ile Leu
 1               5
```